(12) United States Patent
Chakravarty et al.

(10) Patent No.: US 11,591,345 B2
(45) Date of Patent: Feb. 28, 2023

(54) POLYMORPHS AND SOLID FORMS OF (S)-2-((2-((S)-4-(DIFLUOROMETHYL)-2-OXOOXAZOLIDIN-3-YL)-5,6-DIHYDROBENZO[F]IMIDAZO[1,2-D][1,4]OXAZEPIN-9-YL)AMINO) PROPANAMIDE, AND METHODS OF PRODUCTION

(71) Applicant: Genentech, Inc., South San Francisco, CA (US)

(72) Inventors: Paroma Chakravarty, San Francisco, CA (US); Chong Han, Foster City, CA (US); Sean M. Kelly, South San Francisco, CA (US); Karthik Nagapudi, South San Francisco, CA (US); Scott Savage, Burlingame, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 16/875,545

(22) Filed: May 15, 2020

(65) Prior Publication Data

US 2021/0094970 A1    Apr. 1, 2021

Related U.S. Application Data

(62) Division of application No. 15/963,876, filed on Apr. 26, 2018, now abandoned.

(Continued)

(51) Int. Cl.
*C07D 498/04*   (2006.01)
*A61P 35/00*   (2006.01)
(Continued)

(52) U.S. Cl.
CPC ............ *C07D 498/04* (2013.01); *A61P 35/00* (2018.01); *A61P 35/02* (2018.01); *A61P 35/04* (2018.01); *A61K 9/20* (2013.01); *C07B 2200/13* (2013.01)

(58) Field of Classification Search
CPC .......................... C07D 498/04; C07B 2200/13
See application file for complete search history.

(56) References Cited

U.S. PATENT DOCUMENTS 8,242,104 B2   8/2012 Blaquiere et al.
8,343,955 B2   1/2013 Blaquiere et al.
(Continued)

FOREIGN PATENT DOCUMENTS

CN   103476770 A    12/2013
WO   2011/036280 A1   3/2011
(Continued)

OTHER PUBLICATIONS

Peterson et al., "Expanding the scope of crystal form evaluation in pharmaceutical science" J Pharm Pharmaceut Sci 9(3):317-326 (2006).
(Continued)

*Primary Examiner* — Marcos L Sznaidman
*Assistant Examiner* — Rayna Rodriguez
(74) *Attorney, Agent, or Firm* — Zong-Qiang Bill Tian

(57) ABSTRACT

The present invention relates to crystalline polymorph forms of (S)-2-((2-((S)-4-(difluoromethyl)-2-oxooxazolidin-3-yl)-5,6-dihydrobenzo[f]imidazo[1,2-d][1,4]oxazepin-9-yl) amino)propanamide (GDC-0077), having the structure, Formula I:

(Continued)

US 11,591,345 B2
Page 2

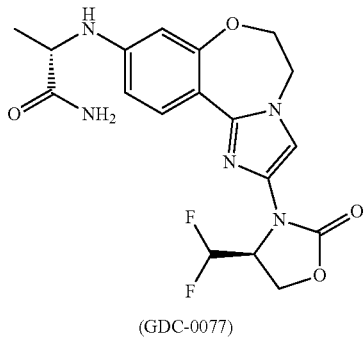

(GDC-0077)

or stereoisomers, geometric isomers, tautomers, and pharmaceutically acceptable salts thereof, and processes of preparing the polymorph forms.

18 Claims, 26 Drawing Sheets

Related U.S. Application Data

(60) Provisional application No. 62/491,812, filed on Apr. 28, 2017.

(51) Int. Cl.
*A61P 35/02* (2006.01)
*A61P 35/04* (2006.01)
*A61K 9/20* (2006.01)

(56) References Cited

U.S. PATENT DOCUMENTS

| | | |
|---|---|---|
| 8,586,574 B2 | 11/2013 | Blaquiere et al. |
| 9,266,903 B2 | 2/2016 | Stults |
| 9,481,690 B2 | 11/2016 | Stults et al. |
| 9,546,178 B2 | 1/2017 | Blaquiere et al. |
| 9,650,393 B2 | 5/2017 | Braun et al. |
| 10,112,932 B2 | 10/2018 | Braun et al. |
| 10,781,219 B2 | 9/2020 | Gosselin et al. |
| 2011/0076292 A1 | 3/2011 | Blaquiere et al. |
| 2017/0015678 A1 | 1/2017 | Braun et al. |
| 2019/0263793 A1 | 8/2019 | Braun et al. |

FOREIGN PATENT DOCUMENTS

| | | |
|---|---|---|
| WO | 2015/091305 A1 | 6/2015 |
| WO | 2017/001645 A1 | 1/2017 |
| WO | 2018/109204 A1 | 6/2018 |

OTHER PUBLICATIONS

Brittain Polymorphism in Pharmaceutical Solids (Polymorphism in Pharmaceutical Dosage Forms), Harry G. Brittain, vol. 95:235-239 (Jan. 1999).

Caira, "Crystalline polymorphism of Organic Compounds" Topics in Current Chemistry, Springer, Berlin, DE 198:163-208 (Jan. 1, 1998).

International Search Report and Written Opinion for International Patent Application No. PCT/EP2018/060820 completed on Jun. 28, 2018.

Edgar et al., "Preclinical characterization of GDC-0077, a specific PI3K alpha inhibitor in early clinical development" Cancer Res. (Proceedings: AACR Annual Meeting 2017; Apr. 1-5, 2017, Washington, D.C.), 77(13 SUPPL Suppl. Abstract 156):1 ( 2017).

Handbook for Production of Organic Compound Crystal: Principles and Know-how "Chapter 4: Pharmaceutical Product Crystallization Method" (English Translation with JP article attached. Alternative translation of book title: Organic Compound Crystal Formulation Handbook: Prinicples and Knowhow), Noriaki Hirayama, Tokyo, Japan:Maruzen Publishing Co., Ltd.,:57-84 (Jul. 25, 2008).

Kojima et al., "Aiming to Improve Efficiency of Crystal Form Selection in Drug Development" Journal of Pharmaceutical Science and Technology, Japan (English Translation with JP article attached. Alternative translation of article title: Making Crystal Form Selection More Efficient in Pharmaceutical Development), 68(5):344-349 (Sep. 1, 2008).

Non-Final Office Action dated Jan. 15, 2020 from U.S. Appl. No. 16/140,392, filed Sep. 24, 2018, Marie-Gabrielle Braun et al., Benzoxazepin Oxazolidinone Compounds and Methods of Use.

Staben et al., "Discovery of GDC-007, a highly isoform selective inhibitor of PI3Ka that promotes selective loss ofmutant-p110a" Cancer Res. (Abstract DDT02-01), 77( SUPPL 13) (Jul. 2017).

U.S. Appl. No. 16/875,537, filed May 15, 2020, Paroma Chakravarty et al., Polymorphs and Solid Forms of (S)-2-((2-((S)-4-(Dlfluoromethyl)-2-Oxooxazolidln-3-YL)-5,6-Dihydrobenzo[F]Imidazo[1,2-D][1,4]Oxazepin-9-YL)Amino)Propanamide, and Methods of Production.

Vippagunta et al., "Cryatlline solids" Adv Drug Deliver Rev 48:3-26 ( 2001).

POLYMORPHS AND SOLID FORMS OF (S)-2-((2-((S)-4-(DIFLUOROMETHYL)-2-OXOOXAZOLIDIN-3-YL)-5,6-DIHYDROBENZO[F]IMIDAZO[1,2-D][1,4]OXAZEPIN-9-YL)AMINO)PROPANAMIDE, AND METHODS OF PRODUCTION

CROSS-REFERENCE TO RELATED APPLICATIONS

This application is a divisional of U.S. application Ser. No. 15/963,876, filed 26 Apr. 2018, which claims the benefit of priority to U.S. Provisional Application No. 62/491,812 filed 28 Apr. 2017, the content of which application is hereby incorporated by reference in its entirety.

FIELD OF THE INVENTION

The invention relates to polymorph forms of a PI3K inhibitor compound GDC-0077, named as (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide. The invention also relates to processes to obtain polymorph forms of GDC-0077.

BACKGROUND OF THE INVENTION

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I P3-kinase, p110 α (alpha) (U.S. Pat. Nos. 5,824,492; 5,846,824; 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press). The PI3 kinase/Akt/PTEN pathway is an attractive target for cancer drug development since such modulating or inhibitory agents would be expected to inhibit proliferation, reverse the repression of apoptosis and surmount resistance to cytotoxic agents in cancer cells (Folkes et al (2008) J. Med. Chem. 51:5522-5532; Yaguchi et al (2006) Jour. of the Nat. Cancer Inst. 98(8):545-556). The PI3K-PTEN-AKT signaling pathway is deregulated in a wide variety of cancers (Samuels Y, et al. (2004) Science 304 (5670):554; Carpten J, et al (2007) Nature; 448:439-444).

GDC-0077, also known by the IUPAC name: (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide, has potent PI3K activity (WO 2017/001645, US 2017/0015678, Edgar K. et al, #156, "Preclinical characterization of GDC-0077, a specific PI3K alpha inhibitor in early clinical development", and Staben. S. #DDT02-0 "Discovery of GDC-0077, a highly isoform selective inhibitor of PI3Kalpha that promotes selective loss of mutant-p110alpha", American Assoc. for Cancer Res. (AACR) annual meeting, Apr. 2, 2017, Washington D.C.), and is being studied in patients with locally advanced or metastatic solid tumors.

Multiple crystal forms with different solid state properties of a drug substance can exhibit differences in bioavailability, shelf life and behavior during processing. Powder X-ray Diffraction is a powerful tool in identifying different crystal phases by their unique diffraction patterns The pharmaceutical industry is often confronted with the phenomenon of multiple polymorphs of the same crystalline chemical entity. Polymorphism is often characterized as the ability of a drug substance, i.e. Active Pharmaceutical Ingredient (API), to exist as two or more crystalline phases that have different arrangements and/or conformations of the molecules in the crystal lattices giving the crystals different physicochemical properties. The ability to be able to manufacture the selected polymorphic form reliably is a key factor in determining the success of the drug product.

Regulatory agencies worldwide require a reasonable effort to identify the polymorphs of the drug substance and check for polymorph interconversions. Due to the often unpredictable behavior of polymorphs and their respective differences in physicochemical properties, consistency in manufacturing between batches of the same product must be demonstrated. Proper understanding of the polymorph landscape and nature of the polymorphs of a pharmaceutical will contribute to manufacturing consistency.

Crystal structure determination at the atomic level and intermolecular interactions offer important information to establish absolute configuration (enantiomers), phase identification, quality control, and process development control and optimization. X-ray Diffraction is widely recognized as a reliable tool for the crystal structure analysis of pharmaceutical solids and crystal form identification.

Availability of a single crystal of the drug substance is preferred due to the speed and accuracy of the structure determination. However, it is not always possible to obtain a crystal of suitable size for data collection. In those cases, the crystal structure can be solved from X-ray powder diffraction data obtained by measurements at ambient conditions and/or at variable temperature or humidity.

SUMMARY OF THE INVENTION

The invention relates to polymorph forms of the PI3K inhibitor GDC-0077 (CAS Registry Number 2060571-02-8, Genentech, Inc.), named as (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide, having the structure, Formula I

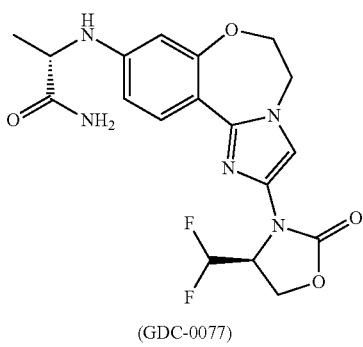

(GDC-0077)

or stereoisomers, geometric isomers, tautomers, and pharmaceutically acceptable salts thereof.

An aspect of the invention is a pharmaceutical composition of a polymorph form of GDC-0077.

An aspect of the invention is a method of treating a hyperproliferative disorder in a mammal with a polymorph form of GDC-0077.

An aspect of the invention is a process for preparing a crystalline polymorph of GDC-0077.

An aspect of the invention is the crystalline, anhydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form A polymorph that exhibits an X-ray powder diffraction pattern having a characteristic peak expressed in degrees 2-theta at approximately 5.7. In some embodiments, the Form A polymorph exhibits an X-ray powder diffraction pattern having characteristic peaks expressed in degrees 2-theta at approximately 5.7, 11.4, and 19.0. In some embodiments, the Form A polymorph exhibits an X-ray powder diffraction pattern having characteristic peaks expressed in degrees 2-theta at approximately 5.7, 11.4, 17.2, 19.0, 19.7, and 24.4.

An aspect of the invention is the crystalline, anhydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form A polymorph that exhibits an X-ray powder diffraction pattern obtained using an incident beam of Cu Kα radiation having a characteristic peak expressed in degrees 2-theta at approximately 5.7; or having characteristic peaks expressed in degrees 2-theta at approximately 5.7, 11.4, and 19.0; or having characteristic peaks expressed in degrees 2-theta at approximately 5.7, 11.4, 17.2, 19.0, 19.7, and 24.4.

An aspect of the invention is the crystalline, anhydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form A polymorph that exhibits an X-ray powder diffraction pattern obtained using an incident beam of Cu Kα (1.541904 Å) radiation generated using Cross Beam optics (40 kV×44 mA) having a characteristic peak expressed in degrees 2-theta at approximately 5.7; or having characteristic peaks expressed in degrees 2-theta at approximately 5.7, 11.4, and 19.0; or having characteristic peaks expressed in degrees 2-theta at approximately 5.7, 11.4, 17.2, 19.0, 19.7, and 24.4.

An aspect of the invention is the Form A polymorph as described herein characterized by the X-ray powder diffraction pattern substantially as shown in FIG. 4.

An aspect of the invention is the Form A polymorph as described herein characterized by the X-ray powder diffraction peaks shown in Table 2.

An aspect of the invention is the Form A polymorph as described wherein a differential scanning calorimetry DSC shows a melting endotherm at approximately 212 to 215° C.

An aspect of the invention is the Form A polymorph as described wherein a differential scanning calorimetry DSC shows a melting endotherm at approximately 214° C.

An aspect of the invention is the Form A polymorph as described herein characterized by the $^{13}$C SSNMR (solid-state nuclear magnetic resonance) spectra substantially as shown in FIG. 7A.

An aspect of the invention is the Form A polymorph as described herein characterized by the $^{19}$F SSNMR (solid-state nuclear magnetic resonance) spectra substantially as shown in FIG. 7B.

An aspect of the invention is a crystalline, anhydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form D polymorph that exhibits an X-ray powder diffraction pattern having characteristic peaks expressed in degrees 2-theta at approximately 7.5, 10.8, 16.8, and 20.4. In some embodiments, the Form D polymorph exhibits an X-ray powder diffraction pattern having characteristic peaks expressed in degrees 2-theta at approximately 7.5, 8.6, 10.8, 16.8, 19.2, and 20.4. In some embodiments, the Form D polymorph as described herein is characterized by the X-ray powder diffraction pattern shown in FIG. 15A. In some embodiments, the Form D polymorph as described herein is characterized by the X-ray powder diffraction peaks shown in Table 3.

An aspect of the invention is a crystalline, anhydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form D polymorph that exhibits an X-ray powder diffraction pattern obtained using an incident beam of Cu Kα radiation having characteristic peaks expressed in degrees 2-theta at approximately 7.5, 10.8, 16.8, and 20.4; or having characteristic peaks expressed in degrees 2-theta at approximately 7.5, 8.6, 10.8, 16.8, 19.2, and 20.4.

An aspect of the invention is a crystalline, anhydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form D polymorph that exhibits an X-ray powder diffraction pattern using an incident beam of Cu Kα (1.541904 Å) radiation generated using Cross Beam optics (40 kV×44 mA) having characteristic peaks expressed in degrees 2-theta at approximately 7.5, 10.8, 16.8, and 20.4; or having characteristic peaks expressed in degrees 2-theta at approximately 7.5, 8.6, 10.8, 16.8, 19.2, and 20.4.

An aspect of the invention is a crystalline, trihydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form B polymorph that exhibits an X-ray powder diffraction pattern having characteristic peaks expressed in degrees 2-theta at approximately 5.4, 10.5, and 25.2. In some embodiments, the Form B polymorph exhibits an X-ray powder diffraction pattern having characteristic peaks expressed in degrees 2-theta at approximately 5.4, 10.5, 19.5, 20.1, 21.6, and 25.2. In some embodiments, the Form B polymorph as described herein is characterized by the X-ray powder diffraction pattern shown in FIG. 12C. In some embodiments, the Form B polymorph as described herein is characterized by the X-ray powder diffraction peaks shown in Table 2 Å.

An aspect of the invention is a crystalline, trihydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form B polymorph that exhibits an X-ray powder diffraction pattern using an incident beam of Cu Kα radiation having characteristic peaks expressed in degrees 2-theta at approximately 5.4, 10.5, and 25.2; or having characteristic peaks expressed in degrees 2-theta at approximately 5.4, 10.5, 19.5, 20.1, 21.6, and 25.2.

An aspect of the invention is a crystalline, trihydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide designated the Form B polymorph that exhibits an X-ray powder diffraction pattern using an incident beam of Cu Kα (1.541904 Å) radiation generated using Cross Beam optics (40 kV×44 mA) having characteristic peaks expressed in degrees 2-theta at approximately 5.4, 10.5, and 25.2; or having characteristic peaks expressed in degrees 2-theta at approximately 5.4, 10.5, 19.5, 20.1, 21.6, and 25.2.

An aspect of the invention is a pharmaceutical composition comprising a therapeutically effective amount of the crystalline, anhydrate polymorph of Form A as described above, and a pharmaceutically acceptable carrier, glidant, diluent, or excipient.

An aspect of the invention is a pharmaceutical composition comprising a therapeutically effective amount of the crystalline, anhydrate polymorph of Form D as described above, and a pharmaceutically acceptable carrier, glidant, diluent, or excipient.

An aspect of the invention is a pharmaceutical composition comprising a therapeutically effective amount of the crystalline, trihydrate polymorph of Form B as described above, and a pharmaceutically acceptable carrier, glidant, diluent, or excipient.

An aspect of the invention is the pharmaceutical composition as described above in the form of a tablet.

An aspect of the invention is the pharmaceutical composition as described above wherein the therapeutically effective amount is from about 1 to about 100 mg.

An aspect of the invention is the pharmaceutical composition as described above wherein the crystalline, anhydrate or trihydrate polymorph is milled.

An aspect of the invention is the process for preparing a crystalline polymorph comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol (with or without water) or n-propanol (with or without water), and then cooling the mixture whereby a Form A crystalline polymorph that exhibits an X-ray powder diffraction pattern having a characteristic peak expressed in degrees 2-theta at approximately 5.7; or having characteristic peaks expressed in degrees 2-theta at approximately 5.7, 11.4, and 19.0; or having characteristic peaks expressed in degrees 2-theta at approximately 5.7, 11.4, 17.2, 19.0, 19.7, and 24.4, is formed. In some embodiments, the process comprises heating a slurry of GDC-0077 in ethanol in the presence of less than 40% (or less than 20%, or less than 10%) of water, and then cooling the mixture whereby forming the Form A polymorph. In some embodiments, the process further comprises seeding the mixture with crystalline GDC-0077 (e.g., a crystalline THF solvate).

An aspect of the invention is the process for preparing a crystalline trihydrate polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide comprising slurring (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in water (e.g., DI water). In some embodiments, the process comprises slurring a Form A polymorph of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in DI water for 4 days at room temperature.

An aspect of the invention is a method for the treatment of cancer in a subject in need thereof comprising administering to the subject an effective amount of a crystalline polymorph of GDC-0077 detailed herein (e.g., crystalline anhydrate Form A, crystalline anhydrate Form D, or crystalline trihydrate Form B), or a pharmaceutical composition comprising a crystalline polymorph of GDC-0077 detailed herein (e.g., crystalline anhydrate Form A, crystalline anhydrate Form D, or crystalline trihydrate Form B), and a pharmaceutically acceptable carrier, glidant, diluent, or excipient. In some embodiments, the cancer is a HR-positive and HER2-negative breast cancel expressing a PIK3CA mutation. In some embodiments, the method further comprises one or more additional therapeutic agents (e.g., fulvestrant, palbociclib and/or letrozole).

An aspect of the invention is a crystalline polymorph of GDC-0077 detailed herein (e.g., crystalline anhydrate Form A, crystalline anhydrate Form D, or crystalline trihydrate Form B), or a pharmaceutical composition comprising a crystalline polymorph of GDC-0077 detailed herein (e.g., crystalline anhydrate Form A, crystalline anhydrate Form D, or crystalline trihydrate Form B), for use in the treatment of cancer. In some embodiment the cancer is a HR-positive and HER2-negative breast cancel expressing a PIK3CA mutation. In some embodiments, the polymorphs for use further comprise one or more additional therapeutic agents (e.g., fulvestrant, palbociclib and/or letrozole). An aspect of the invention is the use of a crystalline polymorph of GDC-0077 detailed herein (e.g., crystalline anhydrate Form A, crystalline anhydrate Form D, or crystalline trihydrate Form B), or a pharmaceutical composition comprising a crystalline polymorph of GDC-0077 detailed herein (e.g., crystalline anhydrate Form A, crystalline anhydrate Form D, or crystalline trihydrate Form B), in the manufacture of a medicament for use in the treatment of cancer. In some embodiment the cancer is a HR-positive and HER2-negative breast cancel expressing a PIK3CA mutation. In some embodiments, the uses further comprise one or more additional therapeutic agents (e.g., fulvestrant, palbociclib and/or letrozole).

An aspect of the invention is the invention as described herein.

DETAILED DESCRIPTION OF EMBODIMENTS OF THE INVENTION

Figure 1:
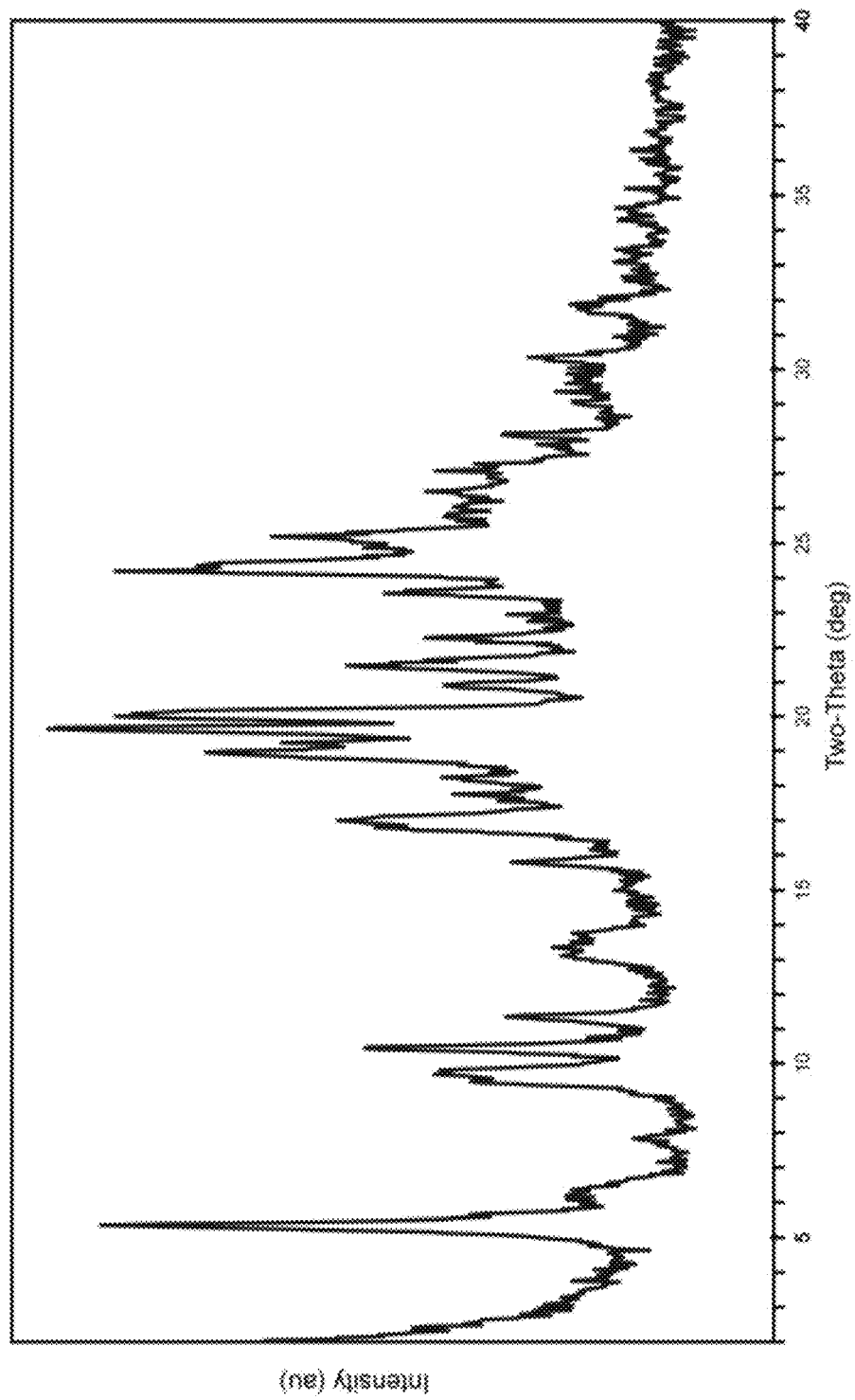
FIG. 1 shows XRPD pattern of starting material GDC-0077.

Unless defined otherwise, technical and scientific terms used herein have the same meaning as commonly understood by one of ordinary skill in the art to which this invention belongs, and are consistent with:

Definitions

The words "comprise", "comprising", "include", "including", and "includes" when used in this specification and claims are intended to specify the presence of stated features, integers, components, or steps, but they do not preclude the presence or addition of one or more other features, integers, components, steps, or groups thereof.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about +−0.2 degrees 2-theta (θ). A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

"Polymorph", as used herein, refers to the occurrence of different crystalline forms of a compound differing in packing or conformation/configuration but with the same chemical composition. Crystalline forms have different arrangements and/or conformations of the molecule in the crystal lattice. Solvates are crystal forms containing either stoichiometric or nonstoichiometric amounts of a solvent. If the incorporated solvent is water, the solvate is commonly known as a hydrate. Hydrates/solvates may exist as polymorphs for compounds with the same solvent content but different lattice packing or conformation. Therefore, a single compound may give rise to a variety of polymorphic forms where each form has different and distinct physical properties, such as solubility profiles, melting point temperatures, hygroscopicity, particle shape, density, flowability, compactability and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffractometry and by other methods such as, infrared or Raman or solid-state NMR spectrometry. For a general review of polymorphs and the pharmaceutical applications of polymorphs see G. M. Wall, Pharm Manuf. 3:33 (1986); J. K. Haleblian and W. McCrone, J. Pharm. Sci., 58:911 (1969); "Polymorphism in Pharmaceutical Solids, Second Edition (Drugs and the Pharmaceutical Sciences)", Harry G. Brittain, Ed. (2011) CRC Press (2009); and J. K. Haleblian, J. Pharm. Sci., 64, 1269 (1975), all of which are incorporated herein by reference.

The acronym "XRPD" means X-ray powder diffraction, an analytical technique which measures the diffraction of X-rays in the presence of a solid component. Materials which are crystalline and have regular repeating arrays of atoms generate a distinctive powder pattern. Materials with similar unit cells will give powder patterns that are similar in position as measured in 020 (theta). Solvates which exhibit this property are called isostructural or isomorphous solvates. The intensity of the reflections varies according to the electron density causing diffraction as well as sample, sample preparation, and instrument parameters. Analysis of XRPD data is based upon the general appearance of the measured powder pattern(s) with respect to the known response of the X-ray diffraction system used to collect the data. For diffraction peaks that may be present in the powder pattern, their positions, shapes, widths and relative intensity distributions can be used to characterize the type of solid state order in the powder sample. The position, shape and intensity of any broad diffuse scatter (halos) on top of the instrumental background can be used to characterize the level and type of solid state disorder. The combined interpretation of the solid state order and disorder present in a powder sample provides a qualitative measure of the macrostructure of the sample.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Polymorphs of GDC-0077

The present invention includes polymorphs of GDC-0077, and processes, methods, and reagents for the production of polymorphs of GDC-0077, shown as Formula I (CAS Registry Number 2060571-02-8):

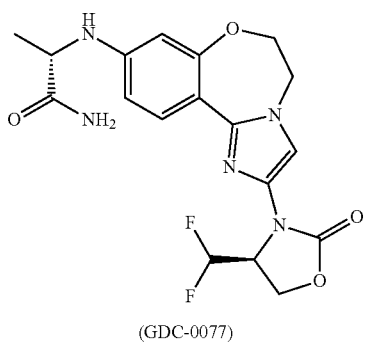

(GDC-0077)

and named as: (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide (WO 2017/001645, US 2017/0015678) which are expressly incorporated by reference). As used herein, GDC-0077 includes all stereoisomers, geometric isomers, tautomers, and pharmaceutically acceptable salts thereof. GDC-0077 is the API (Active Pharmaceutical Ingredient) in formulations being developed for the clinical treatment of breast cancer and other disorders.

X-Ray Powder Diffraction Analysis

Analysis of X-ray Powder Diffraction (XRPD) patterns was conducted with commercially available, analytical software. XRPD is useful for fingerprinting of different crystalline phases, polymorphs, hydrates or solvates by their unique diffraction pattern. Along the abscissa (horizontal axis) is plotted the so-called 2Theta values—the series of angles between the incident and diffracted beams. The ordinate (vertical axis) records the intensity of the scattered X-ray registered by detector. The set of peaks act as a unique fingerprint of the crystallogaphic unit cell within a crystalline substance. The crystallographic unit cell is the smallest atomic-scale 3D fragment that is repeated periodically in three dimensions throughout the entire crystal. All crystalline substances are distinguished by their crystallographic unit cells (and therefore peak positions). By comparing measured peak positions with those held in a database, the crystalline substance may be identified uniquely. For pure substances, the positions of all peaks are generally a function of three parameters: a,b,c and three angles: alpha, beta, gamma ($\alpha$, $\beta$, $\gamma$) defining the elementary parallelepiped that constitutes the crystallographic unit cell.

Figure 2:
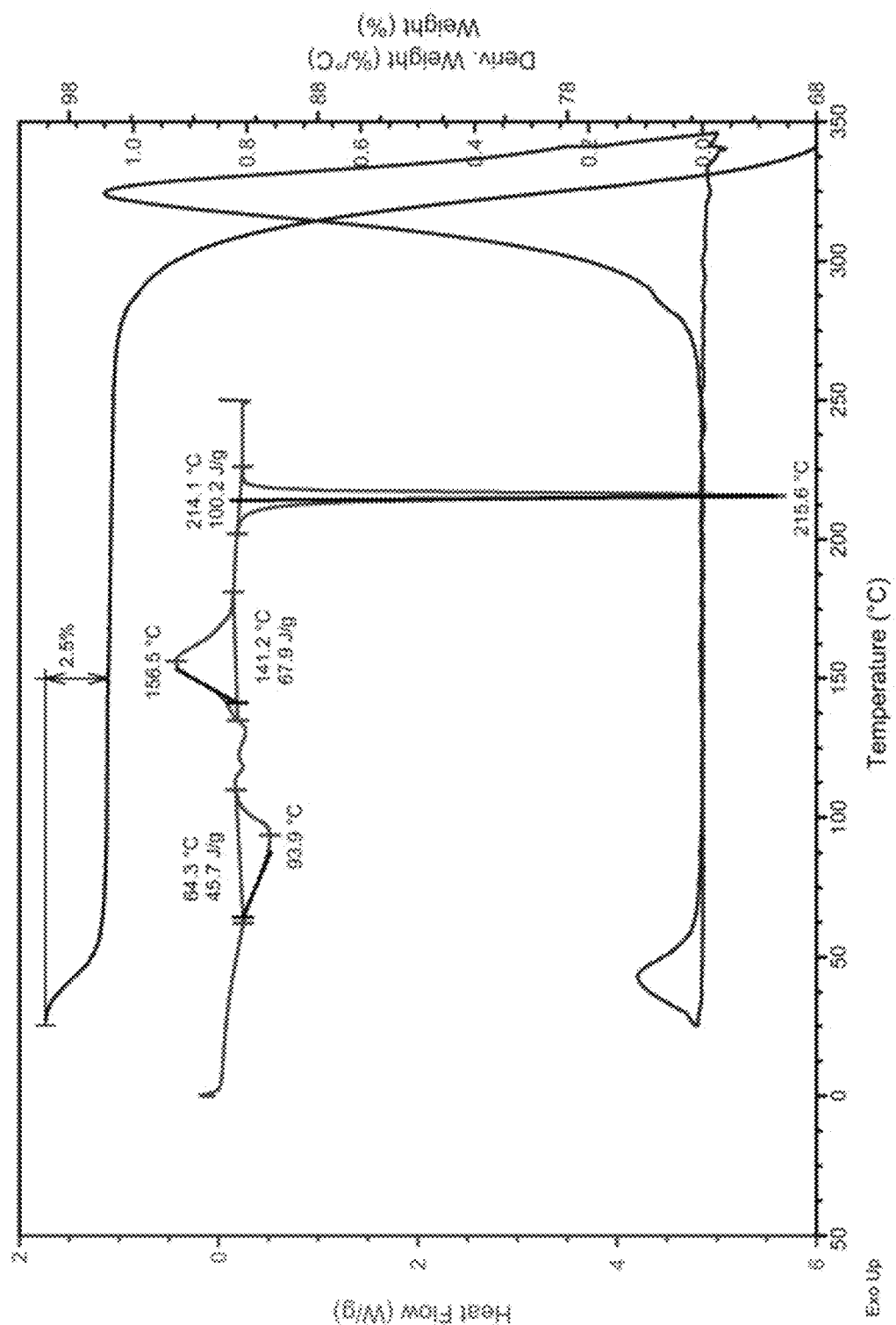
FIG. 2 shows DSC and TGA traces of starting material GDC-0077. The desolvation/vaporization endotherm and the recrystallization endotherm occur at 64 and 141° C. respectively (onset), followed by the melting endotherm at 214° C. TGA shows a weight loss of ~2.5% w/w before the melting event.

The XRPD pattern of GDC-0077 as starting material, prepared as in Example 1, is shown in FIG. 1. As evident from the increased baseline counts and poorly resolved diffraction peaks, the starting material is poorly crystalline. FIG. 2 shows DSC (Differential Scanning Calorimetry) and TGA (Thermogravimetry) traces of starting material GDC-0077. The desolvation/vaporization endotherm and the recrystallization endotherm occur at 64 and 141° C. respectively (onset), followed by the melting endotherm at 214° C. TGA shows a weight loss of ~2.5% w/w before the melting event. The TGA data (FIG. 2) shows a weight loss of 2.5% by 150° C. The DSC thermogram shows a sharp melting endotherm with an extrapolated onset of ~214° C. preceded by a prominent shallow endotherm (possibly desolvation/vaporization) and an exotherm (crystallization/rearrangement/phase transformation) in the 50-175° C. range. The desolvation/vaporization endotherm and the recrystallization endotherm occur at 64 and 141° C. respectively (onset), followed by the melting endotherm at 214° C. TGA shows a weight loss of ~2.5% w/w before the melting event.

Figure 3:
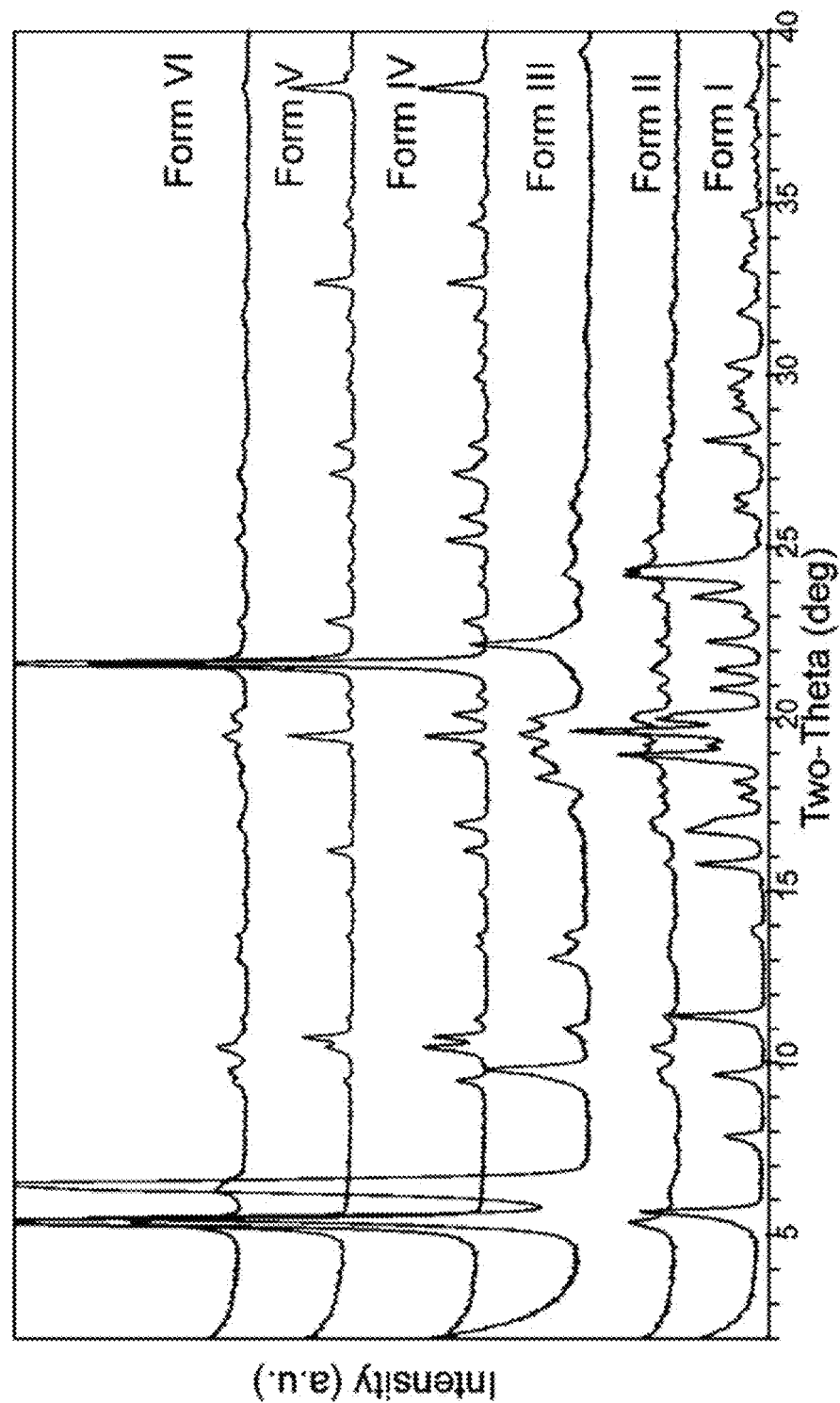
FIG. 3 shows overlay of the XRPD patterns of the different solid form hits, Forms 1-VI, obtained in the 96 well HTS polymorph screening for GDC-0077.

XRPD patterns of several different solid form hits obtained from the full plate (96 well) high throughput screening, as detailed in Example 2. FIG. 3 shows overlay of the XRPD patterns of the different solid form hits, Forms 1-VI, obtained in the 96 well HTS polymorph screening for GDC-0077. The two most frequently obtained forms were Forms I and II, of which Form II matched the starting material (FIG. 3). Several other new polymorph hits were identified from the evaporation, precipitation and cooling plates which were scaled up 10x fold, i.e. 150-200 mg each for further characterization. Table 1 summarizes the scale up condition for six different forms I-VI.

TABLE 1

Scale up conditions for high throughput screening polymorph hits for GDC-0077

| Form | Crystallization conditions |
|---|---|
| I | Slurry in ethanol (200 proof) at 50° C. for 4 hrs, cooled to RT and evaporate dusing nitrogen purge |
| II | Slurry at 50° C. for 4 hrs in water-DMA mixture (4:1 v/v), followed by evaporation (RT) |
| III | Slurry at 50° C. for 2 hrs in water-THF mixture (1:1 v/v), filter solution and cool saturated solution from 50 to 20° C. (controlled cooling), evaporate dusing nitrogen purge (2-3 hrs) followed by overnight evaporation (RT) |
| IV | Slurry at 50° C. for 2 hrs in water-ethanol (3:7, v/v), filter saturated solution into 2X volume ethanol (anti-solvent), cooled to RT, evaporated using nitrogen purge (2-3 hrs) followed by overnight evaporation (RT) |
| V | Slurry at 50° C. for 2 hrs in water-acetone mixture (3:7 v/v), filter solution followed by evaporation using nitrogen purge (2-3 hrs) and overnight evaporation (RT) |
| VI | Slurry at 50° C. for 2 hrs in DCE-MeNO2 mixture (4:1 v/v), filter saturated solution into 2X volume ethanol (anti-solvent), cooled to RT, evaporated using nitrogen purge (2-3 hrs) followed by overnight evaporation (RT) |

GDC-0077 Solid Forms

Figure 4:
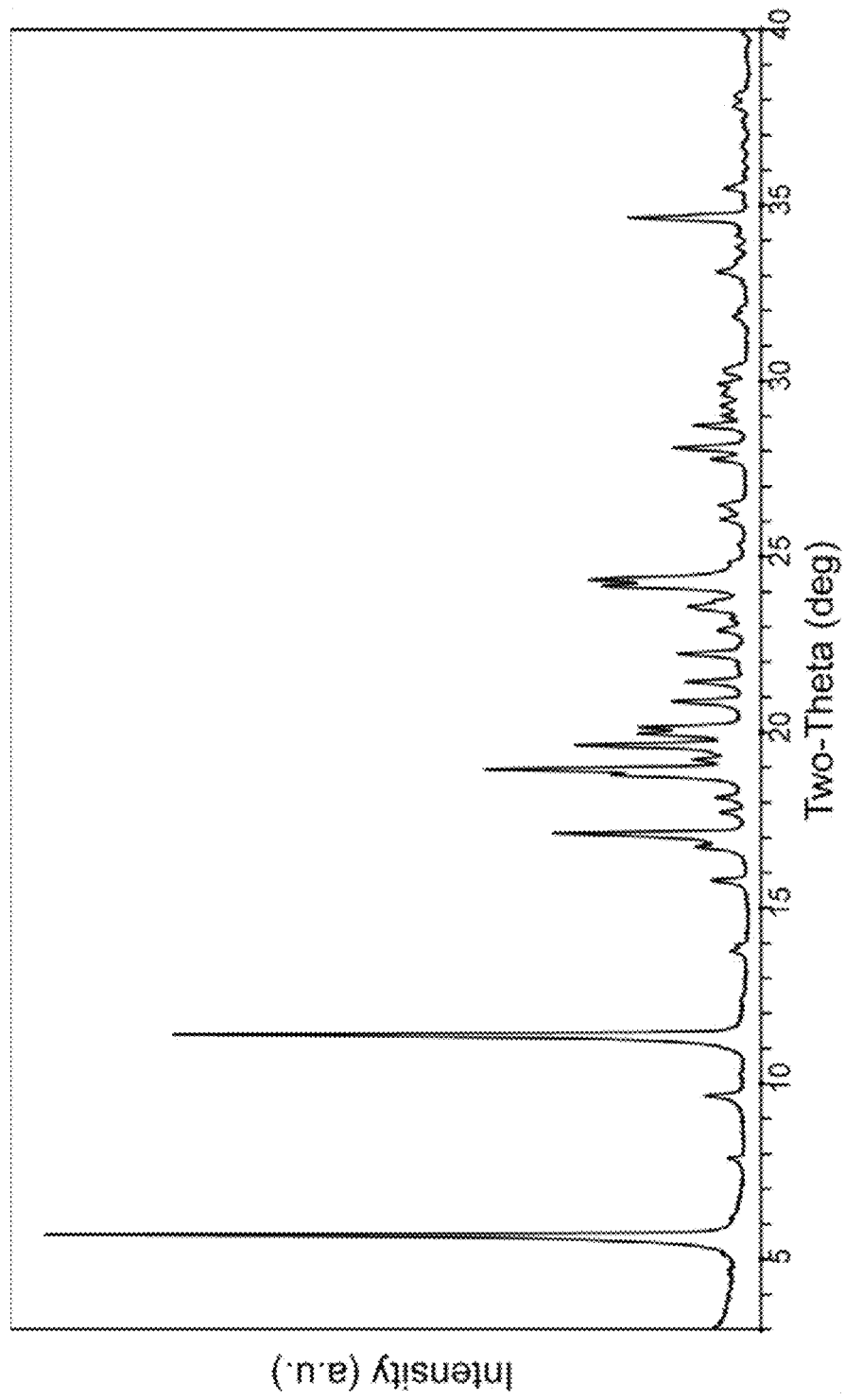
FIG. 4 shows XRPD of anhydrous Form I (Form A) GDC-0077.
Figure 5A:
FIG. 5A shows SEM image at 1000× magnification (benchtop Phenom SEM (Nanoscience Instruments, Inc., AZ) of anhydrous Form I (Form A) GDC-0077.
Figure 5B:
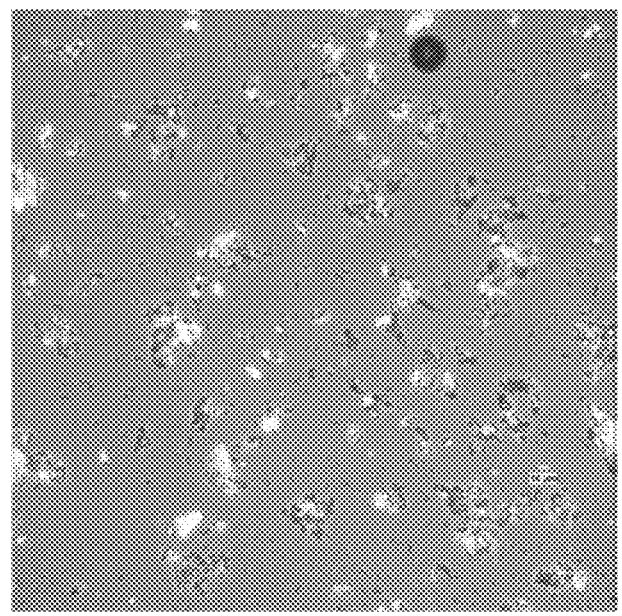
FIG. 5B shows PLM image (Leica DM 4000B microscope equipped with a high resolution CCD camera and motorized stage (Clemex Technologies Inc., Longueuil, Quebec, Canada) at 200× magnification) of anhydrous Form I (Form A) GDC-0077.
Figure 6A:
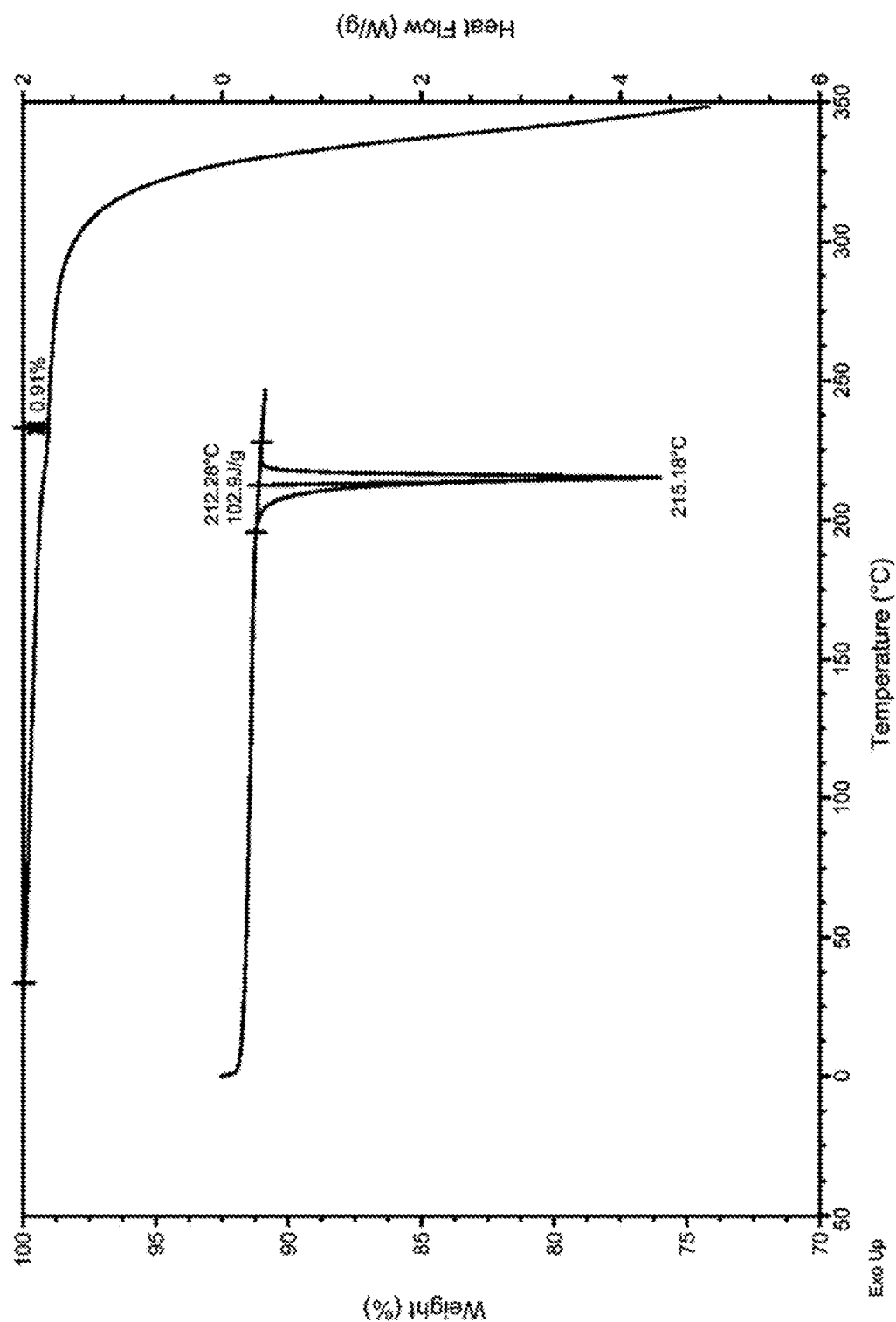
FIG. 6A shows Thermal analysis of anhydrous Form I (Form A) GDC-0077.

FIG. 4 shows XRPD of anhydrous Form I (Form A) GDC-0077. Table 2 shows the XRPD Peak Search Report for GDC-0077 Form I/A. FIG. 5A shows Scanning electron microscopy (SEM) at 1000× magnification of anhydrous Form I (Form A) GDC-0077. FIG. 5B shows Polarized light microscopy (PLM) at 200× magnification of anhydrous Form I (Form A) GDC-0077. Form I was found to be substantially crystalline with small, rod shaped crystals of 30-40 μm (microns) in length. Thermal analysis of anhydrous Form I (Form A) GDC-0077 shows negligible weight loss by TGA (~0.25% w/w) and a melting endotherm at 214° C. by DSC and was thus deemed anhydrous (FIG. 6A). Water sorption at 25° C., using the rigorous protocol of rate of change of mass (dm/dt), showed a negligible moisture uptake of <0.3% w/w over the experimental time scale (Example 5). Since Form I was reasonably well characterized to be an anhydrous, crystalline form, it is referred to as Form A.

TABLE 2

XRPD Peak Search Report for GDC-0077 Form I/A

| 2-Theta | d(Å) | BG | Height | H % |
|---|---|---|---|---|
| 5.734 | 15.3997 | 1099 | 93701 | 100.0 |
| 11.434 | 7.7324 | 1215 | 76458 | 81.6 |
| 17.162 | 5.1625 | 1535 | 25735 | 27.5 |
| 19.000 | 4.6671 | 1692 | 35455 | 37.8 |
| 19.684 | 4.5064 | 1692 | 19728 | 21.1 |
| 20.184 | 4.3959 | 1692 | 13315 | 14.2 |
| 24.390 | 3.6466 | 2257 | 20616 | 22.0 |
| 28.142 | 3.1683 | 2003 | 10879 | 11.6 |
| 34.681 | 2.5844 | 2243 | 18146 | 19.4 |

Table 2 shows a Peak Search Report for GDC-0077, marker peaks of the substantially crystalline Form I/A, with 31 Peaks, Max P/N=152.2), from the XRPD of FIG. 4: GMP Lot @Phi=136.1. PEAK: 13(pts)/Parabolic Filter, Threshold=2.0, Cutoff=5.0%, BG=3/1.0, Peak-Top=Summit.

Figure 6B:
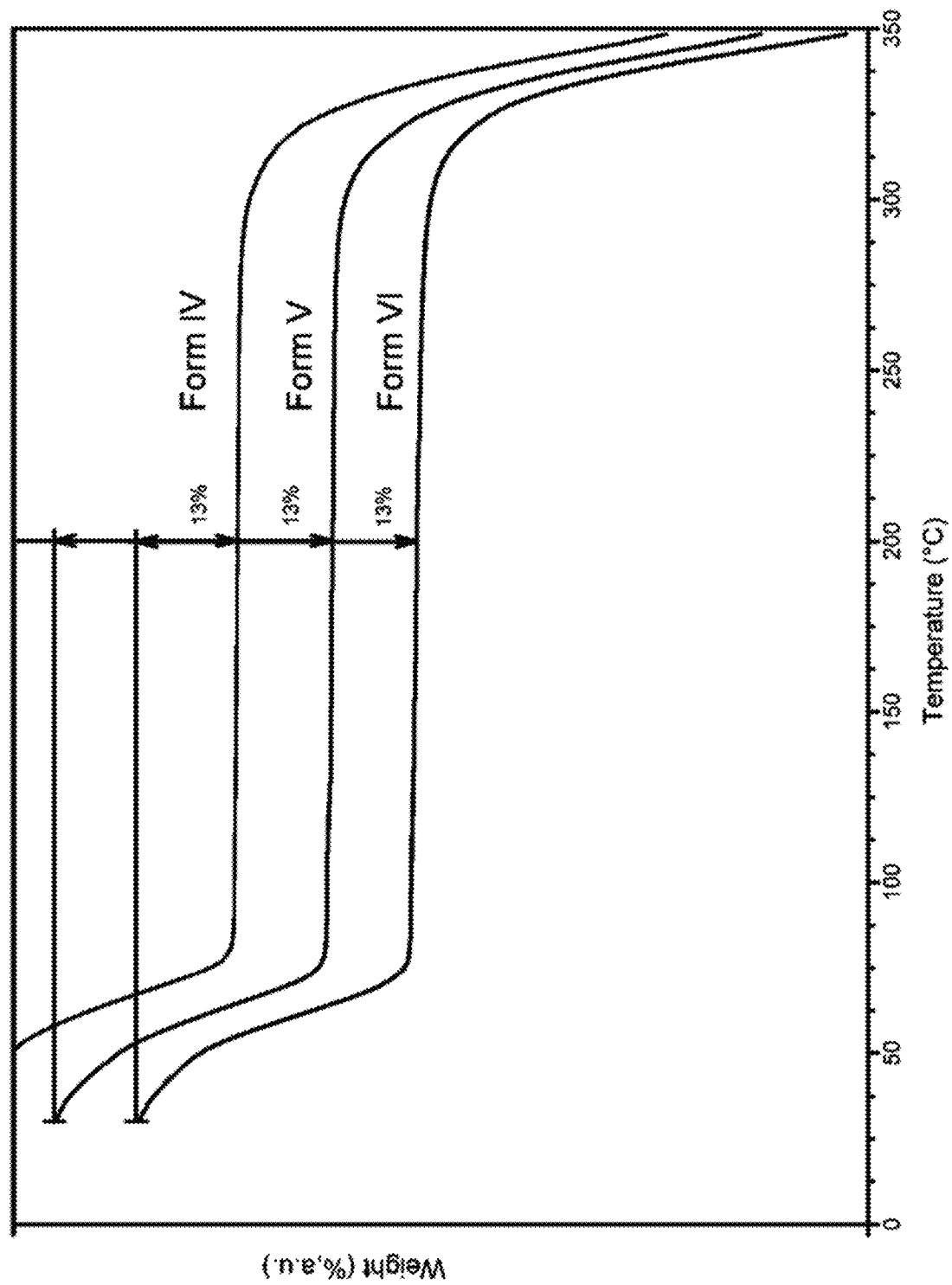
FIG. 6B shows TGA of Forms IV-VI.
Figure 6C:
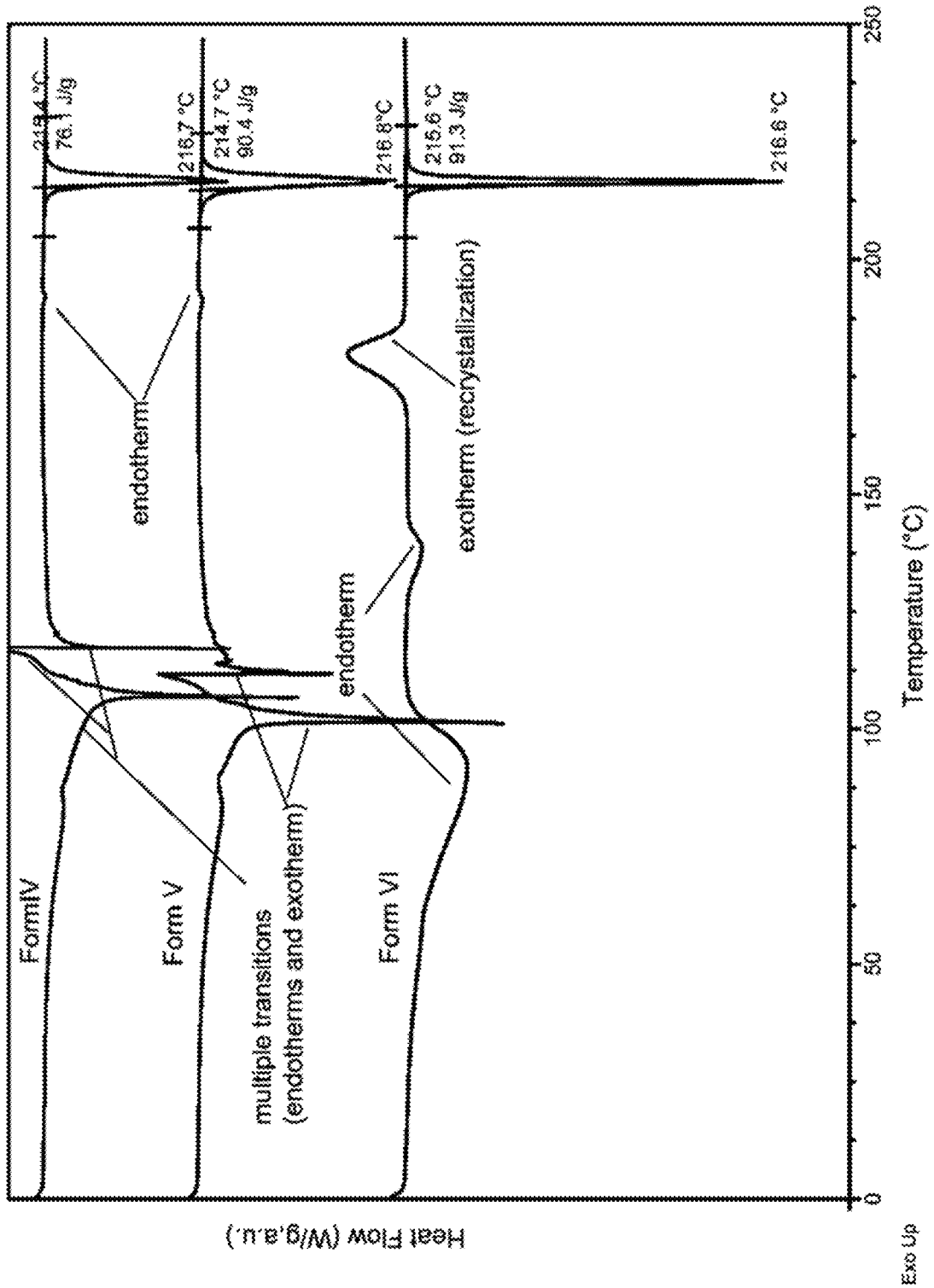
FIG. 6C shows DSC of Forms IV-VI. Multiple transitions, attributable to desolvation, formation of metastable form and subsequent conversion to Form A and its melting, were observed in the DSC traces and have been indicated.
Figure 6D:
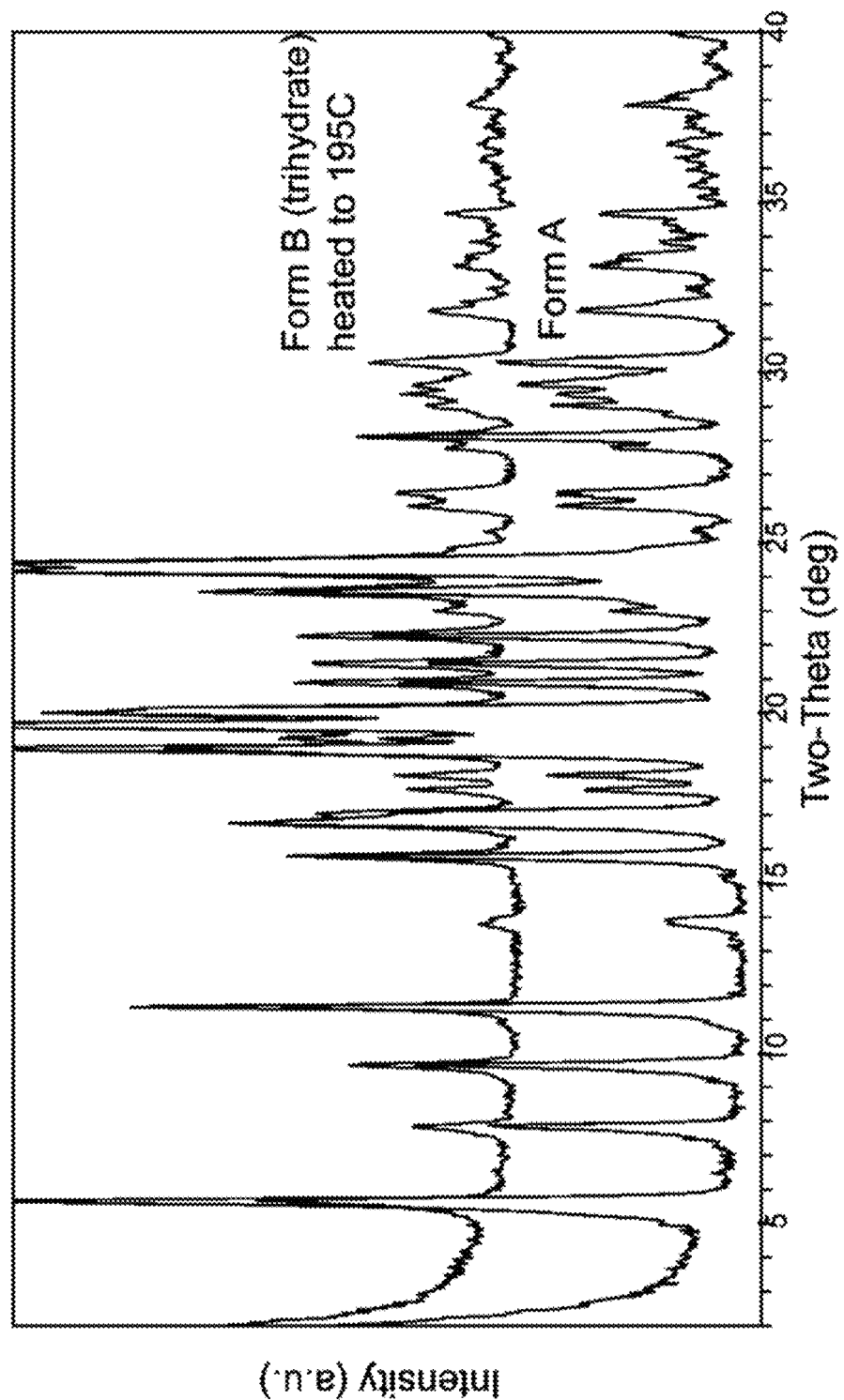
FIG. 6D shows XRPD of product phase obtained upon heating Form B (trihydrate) to 195° C., with Form A pattern included for comparison. As indicated, the trihydrate ultimately converts to anhydrous Form A at this temperature.

Forms IV-VI appeared similar by XRPD (FIG. 3) with differences in relative peak intensities in the 5-20° 2θ range. These three forms showed a weight loss of 13% w/w up to 150° C. by TGA (FIG. 6B), and multiple transitions up to the melting point at 214° C. by DSC (FIG. 6C). These transitions are speculated to be solvent loss (first endotherm, 88° C. for Forms IV and V) followed by crystallization of intermediate form and its subsequent melting/conversion to Form A, which melts at 214° C. Form VI shows a similar trend of desolvation followed by a recrystallization exotherm to Form A by DSC. Multiple transitions, attributable to desolvation, formation of metastable form and subsequent conversion to Form A and its melting, were observed in the DSC traces. These transitions are outlined in FIG. 6C. The qNMR data for residual solvents determined these forms to be hydrates with water content ranging from 13.4-13.8% w/w, which matched closely with the weight loss observed via TGA. All three forms were heated up to 195° C. in the TGA and analyzed by XRPD and the product phase was confirmed to be Form A, the final stable anhydrous form (FIG. 6D). Since all three forms were found to be stoichiometrically the same with very similar XRPD patterns varying only in relative intensity of the diffraction peaks, they were considered to be the same form, i.e. a trihydrate (3 moles of water/mole of anhydrate) which will be henceforth referred to as Form B. The XRPD of obtained upon heating Form B (trihydrate) to 195° C., indicated, the trihydrate ultimately converts to anhydrous Form A at this temperature.

Figure 9:
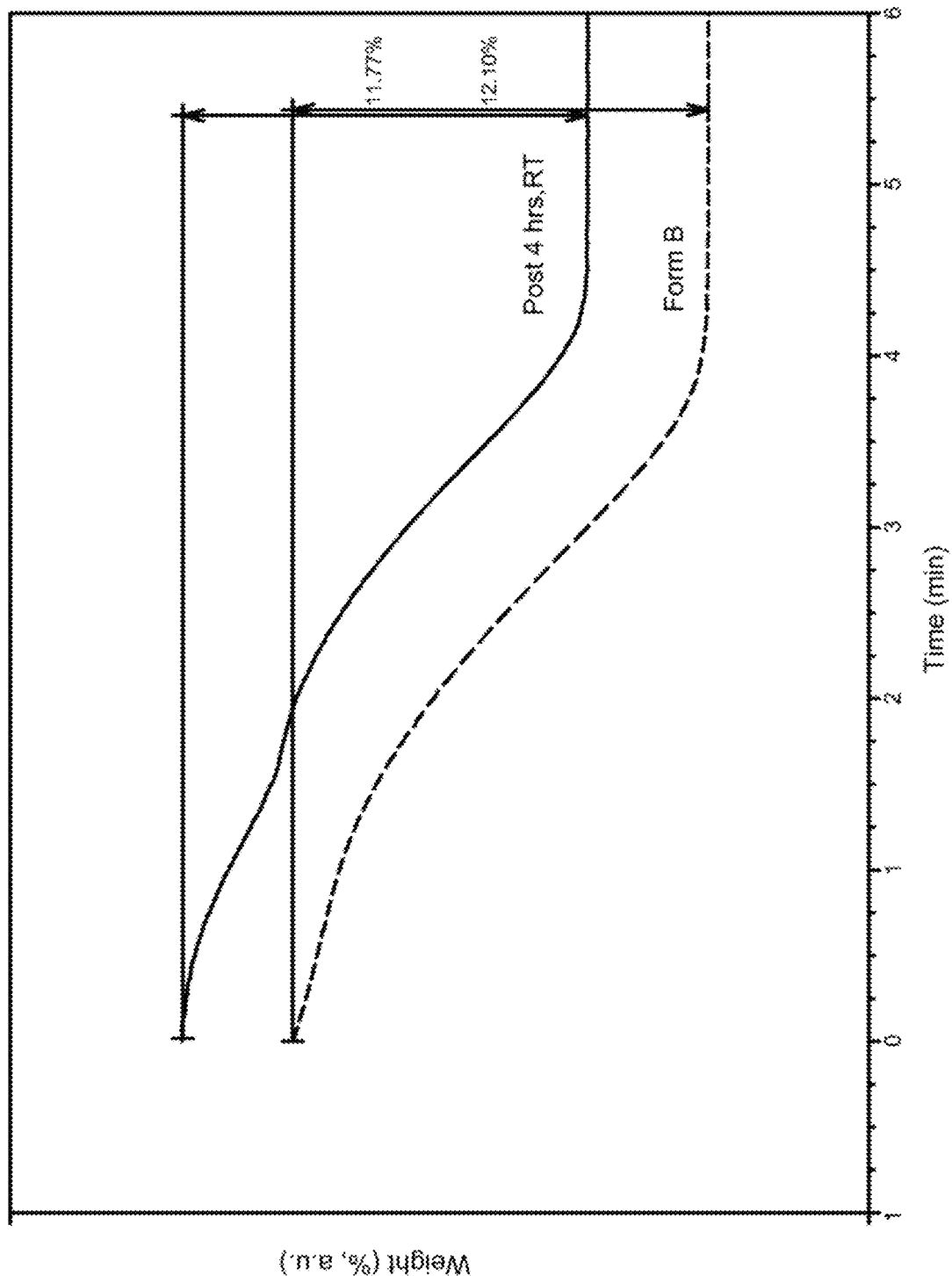
FIG. 9 shows Isothermal TGA traces of trihydrate Form B GDC-0077 before and after equilibration at RT at 60° C.
Figure 10A:
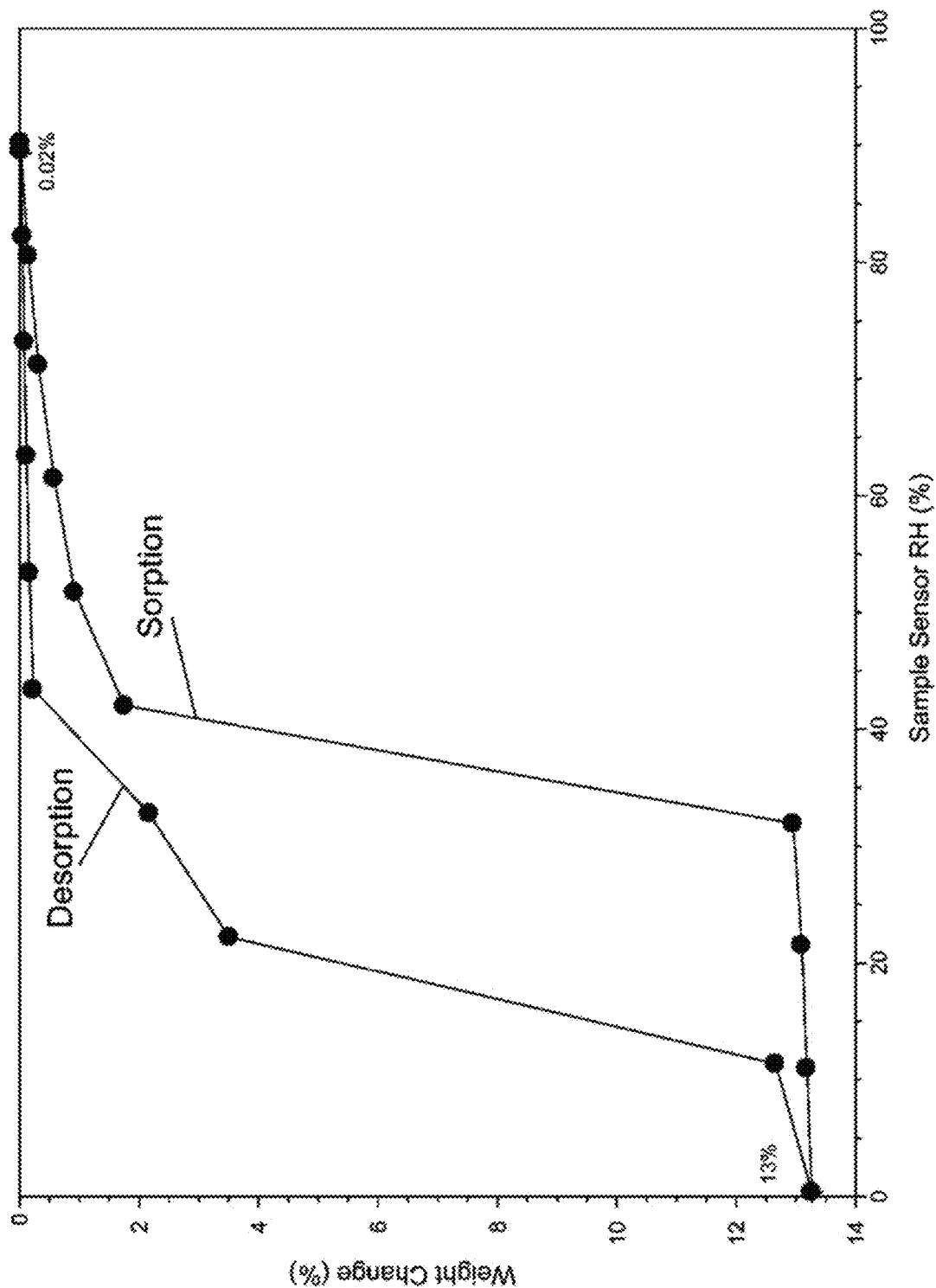
FIG. 10A shows Water sorption behavior of trihydrate Form B GDC-0077 at 25° C.

The desolvation behavior of Form B as well its ability to rehydrate was further characterized. The compound was thus held isothermally in TGA at 60° C. till the weight loss was found to be constant, followed by equilibration of the desolvated solid at RT at 4 hrs, after which the experiment was repeated. FIG. 9 shows the isothermal dehydration and the weight loss profile of the equilibrated solid. In particular, FIG. 9 shows Isothermal TGA traces of trihydrate Form B GDC-0077 before and after equilibration at RT at 60° C. As evident from the data, the hydrate dehydrates readily, losing almost all of its lattice water (12%) at 60° C. and rehydrates after 4 hours of equilibration which indicates easy passage of water in and out of the lattice. The water sorption desorption behavior of trihydrate Form B GDC-0077 at 25° C. is depicted in FIG. 10A. The dynamic vapor sorption experiment provides information about the dehydration behavior of Form B. Dehydration of Form B commences rapidly below 40% RH (desorption curve) and is complete by the time the sample is exposed to 0% RH. Although there is a hysteresis showing equilibrium lag, the anhydrous product rehydrates beyond 40% RH, equally readily. Unlike the resorption curve where the anhydrous form shows a clear "jump" indicating anhydrous-trihydrate conversion beyond 40% RH, desorption appears to be stepwise, with an intermediate dehydrated form evident between 20-50% RH. The trihydrate dehydrates in 2-3 steps whereas the anhydrate to hydrate formation occurs majorly in one step at >40% RH (25° C.).

Figure 10B:
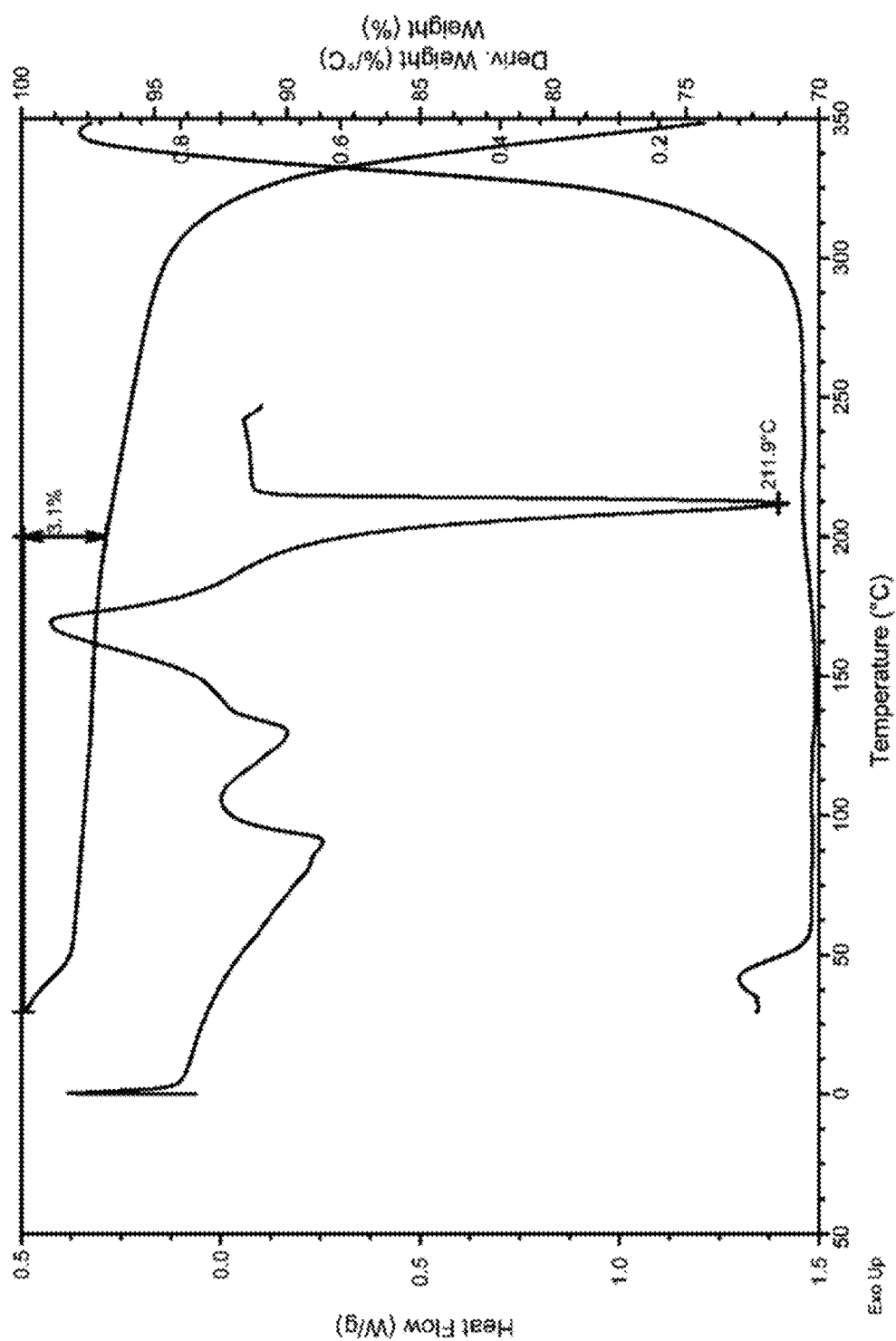
FIG. 10B shows DSC and TGA of Form III.
Figure 11:
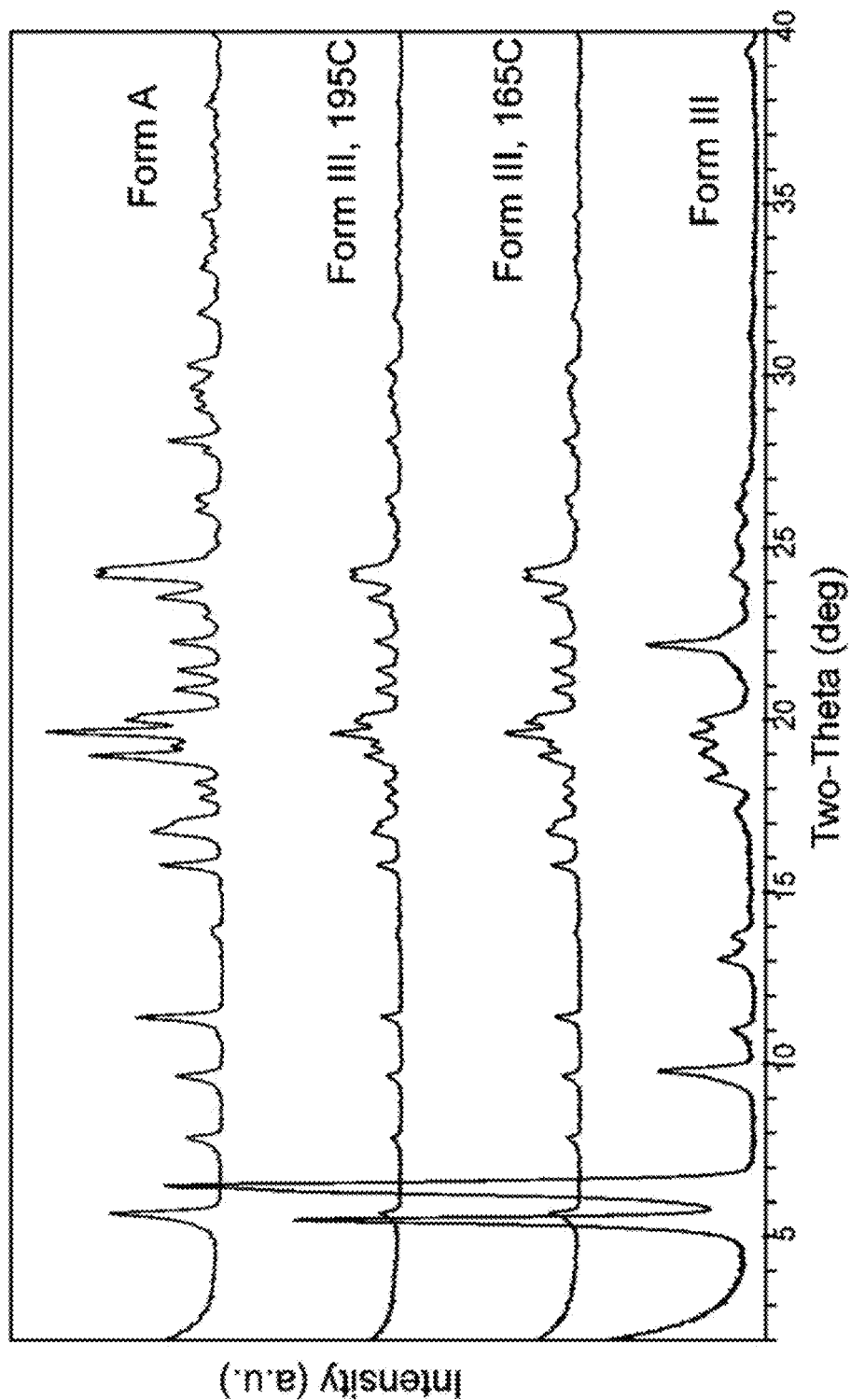
FIG. 11 shows overlay of the XRPD patterns of Form A and Form III solid forms. XRPD patterns of Form III at RT, and when heated to 165 and 195° C. are shown. At higher temperatures (>165 C), Form III/C converts to Form I/A.

The XRPD of Form III was different from Forms IV-VI (FIG. 3). The thermal analysis DSC and TGA traces of Form III in FIG. 10B shows several transitions (desolvation/vaporization endotherm), similar to Form B in FIG. 6C, followed by recrystallization exotherm and melting of the final form, which was confirmed to be Form A by XRPD (FIG. 11). FIG. 11 shows overlay of the XRPD patterns of Form A and Form III solid forms. XRPD patterns of Form III at RT, and when heated to 165 and 195° C. are shown. Form III converts to Form A upon heating at ≥165° C. (FIG. 11). Although Form III showed only a 3% w/w weight loss by TGA, its water content was found to be 11% by qNMR. Form II, on the other hand, was found to be the same as the starting material characterized in FIGS. 1 and 2. Substantial similarity was observed upon comparison of the XRPD patterns of Form II, Form III and the product phase obtained upon isothermal dehydration of Form B at 60° C., indicating that Forms II and III are simply partially desolvated intermediates of Form B, and differing only in their degrees of desolvation. Form is the partially dehydrated intermediate of Form B trihydrate. The possibility of existence of an intermediate hydrate form is also suggested from the step wise desorption profile of Form B (FIG. 10A). For the convenience of nomenclature, Forms II/III (partially dehydrated form) are referred to as Form C. At higher temperatures (>165 C), Form III/C converts to Form I/A.

Figure 12A:
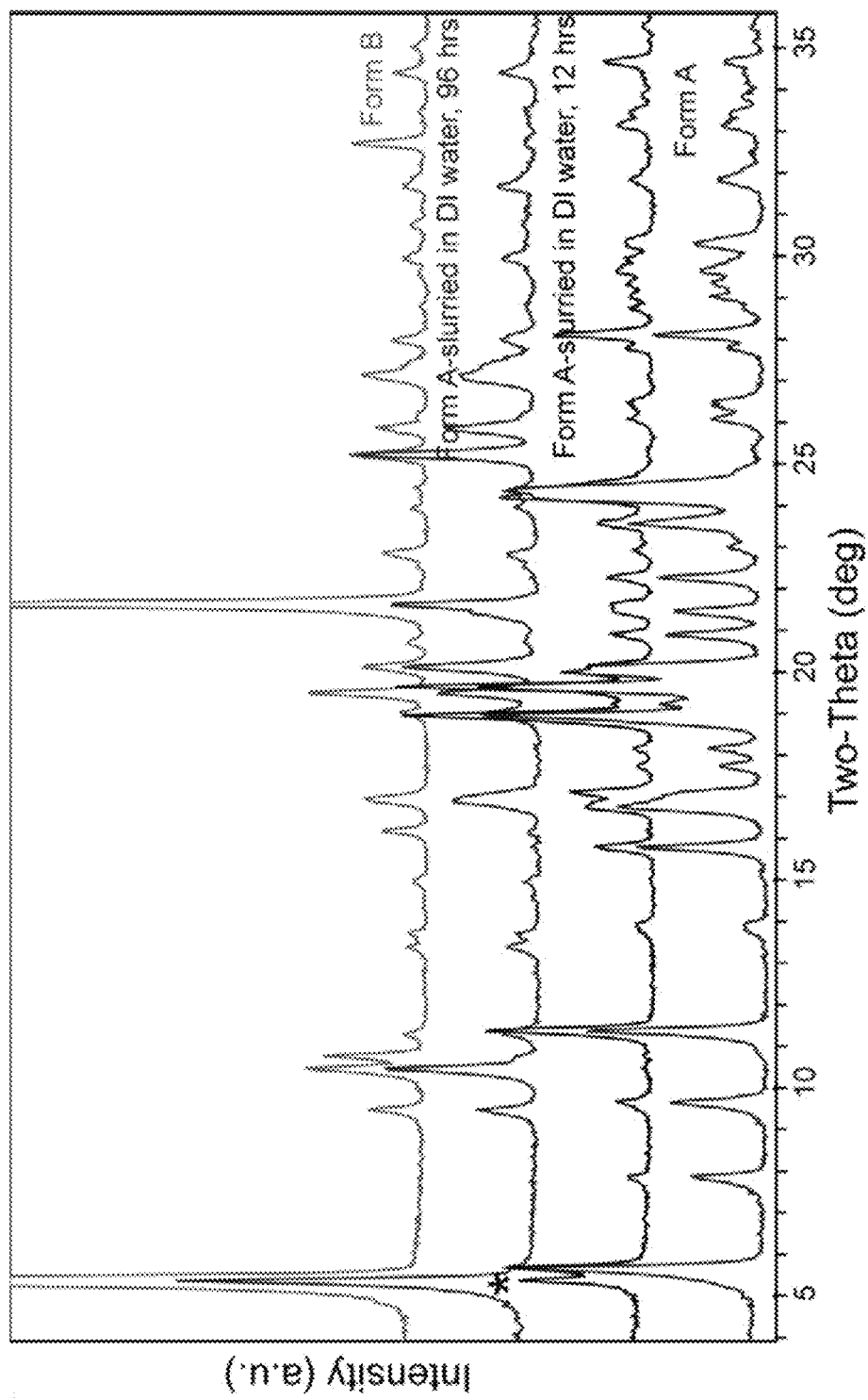
FIG. 12A shows anhydrate (Form A) to hydrate (Form B) conversion upon slurring in DI water for 4 days. Conversion starts within 12 hrs as indicated by hydrate marker peak (*) appearing in the anhydrate XRPD pattern. Form conversion is complete by 96 hrs. XRPD pattern of Form B is included for reference.

It is evident from characterization of trihydrate (Form B) that it desolvates to Form A upon exposure to higher temperature and/or low relative humidity (RH) as seen in FIGS. 9, 10A, and 6D. Conversion of anhydrous Form A to Form B was investigated. Dynamic Vapor sorption (DVS) experiments do not represent thermodynamic conditions since they are conducted on a shorter time scale where equilibrium may not be attained. To check for hydrate formation, Form A was slurried in DI water for 4 days (RT). Form conversion (anhydrate to hydrate) was initiated at 12 hours and was complete within 4 days, as detected by XRPD with reference to Form B. Anhydrate (Form A) to hydrate (Form B) conversion was measured upon slurrying in DI water for 4 days. FIG. 12A shows conversion starts within 12 hrs as indicated by a hydrate marker peak at about 5.5 Two Theta (deg) appearing in the anhydrate XRPD pattern. Form conversion is complete by 96 hrs.

Figure 12B:
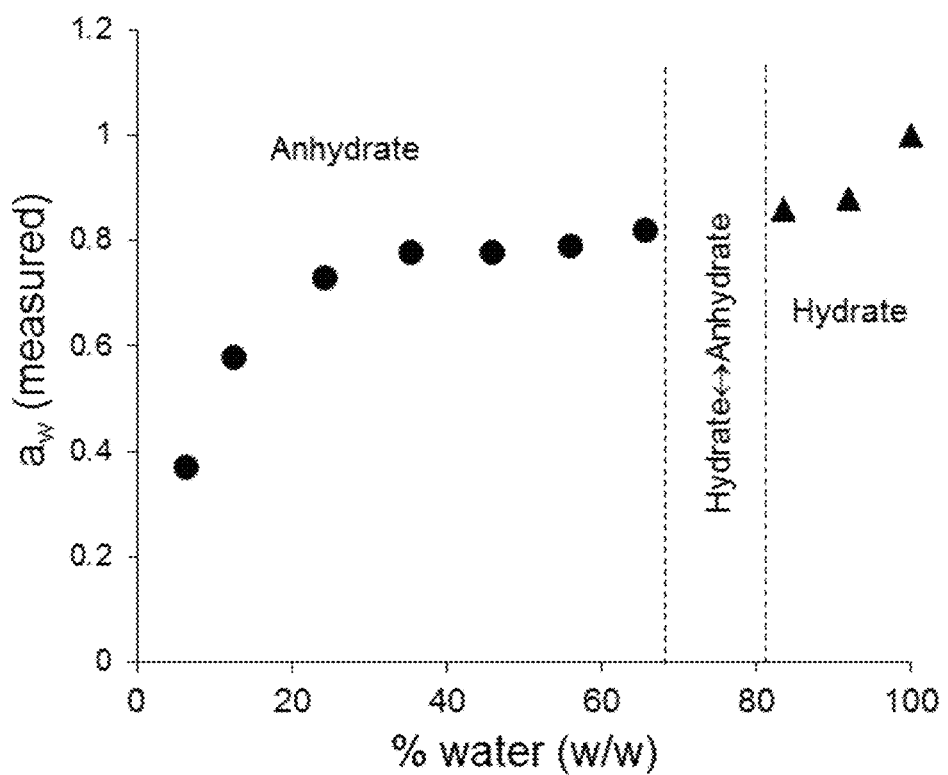
FIG. 12B shows Slurry bridging experiment data for GDC-0077 hydrate-anhydrate system in ethanol-water mixtures at RT (room temperature). The equilibrium RH (relative humidity) zone for the two forms was identified as 82-86%, equivalent to 65-83% w/w water content.

FIG. 12B summarizes the results of the slurry bridging experiments of hydrate-anhydrate mixtures, where the water activity is plotted against the vehicle composition (% water, v/v). FIG. 12B shows slurry bridging experiment data for GDC-0077 hydrate-anhydrate system in ethanol-water mixtures at RT (room temperature). The equilibrium RH (relative humidity) zone for the two forms was identified as 82-86%, equivalent to 65-83% w/w water content. The anhydrous form (Form A) was found to be stable up to water activity ($a_w$) of 0.82, whereas the hydrate (Form B) was found to be the stable form at $a_w$>0.86. Thus the $a_w$ of anhydrate-hydrate equilibrium lies in the 0.82-0.86 range.

XRPD patterns of the solid forms obtained at these different water activities showed anhydrate/Form A remains stable up to 0.82 $a_w$, while the hydrate/Form B is stable at $a_w \geq 0.86$.

Figure 12C:
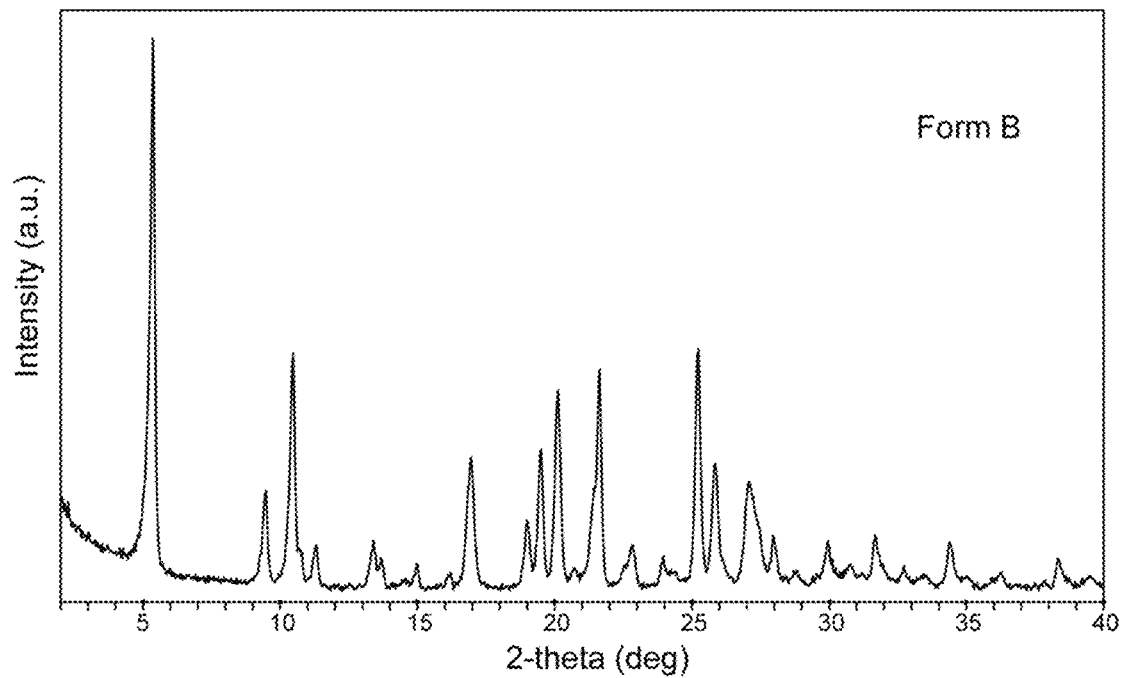
FIG. 12C shows XRPD of trihydrate Form B GDC-0077.

FIG. 12C shows XRPD of trihydrate Form B GDC-0077. Table 2A shows the XRPD Peak Search Report for GDC-0077 Form B.

TABLE 2A

XRPD Peak Search Report for GDC-0077 trihydrate Form B

| 2-Theta | d(Å) | BG | Height | H % |
|---|---|---|---|---|
| 5.359 | 16.4771 | 162 | 3466 | 100.0 |
| 9.470 | 9.3316 | 137 | 574 | 16.6 |
| 10.470 | 8.4424 | 136 | 1467 | 42.3 |
| 16.958 | 5.2242 | 115 | 813 | 23.5 |
| 19.511 | 4.5460 | 100 | 877 | 25.3 |
| 20.118 | 4.4102 | 100 | 1260 | 36.4 |
| 21.634 | 4.1045 | 112 | 1381 | 39.8 |
| 25.234 | 3.5265 | 148 | 1474 | 42.5 |

Figure 13A:
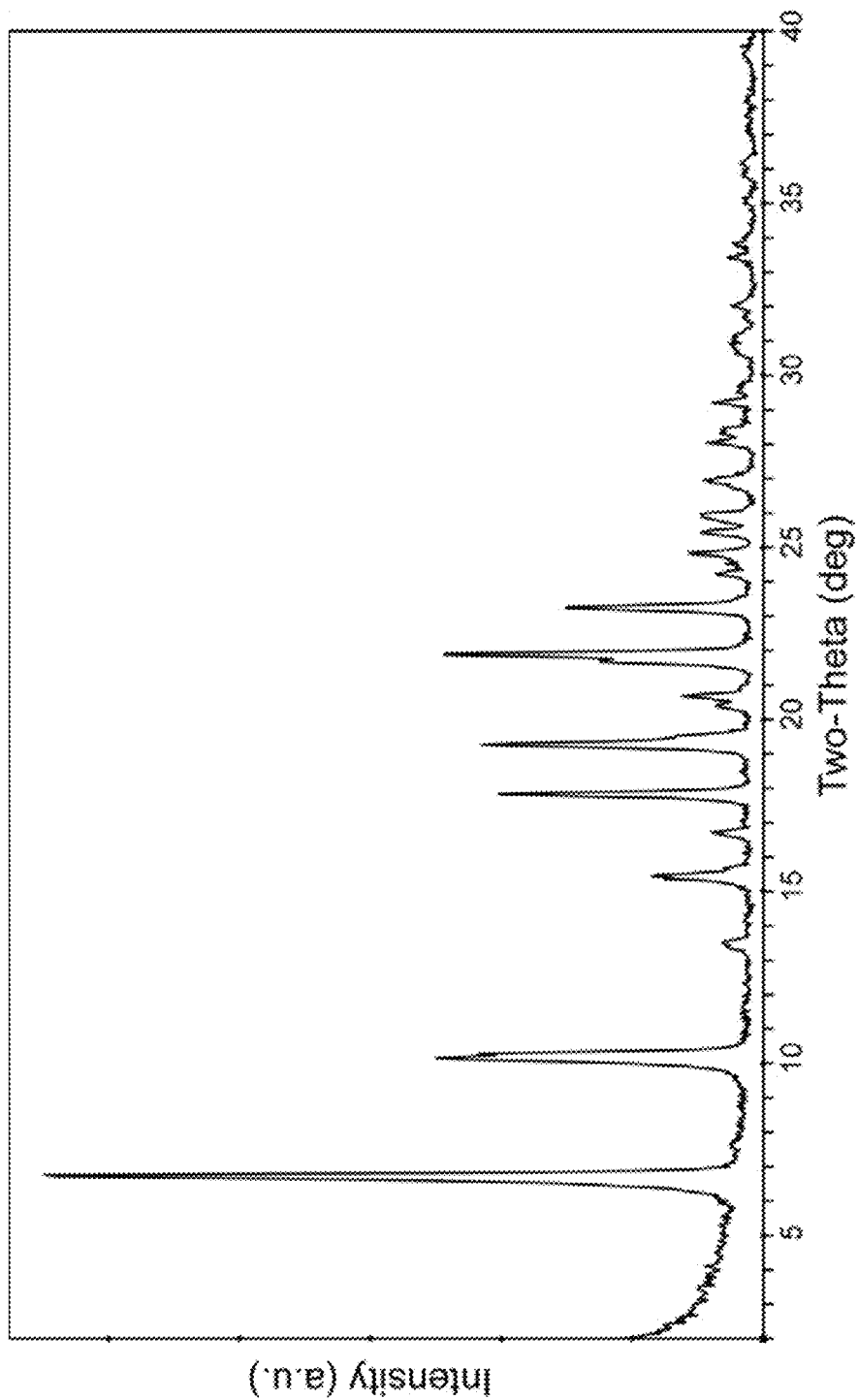
FIG. 13A shows XRPD of GDC-0077 THF solvate.
Figure 13B:
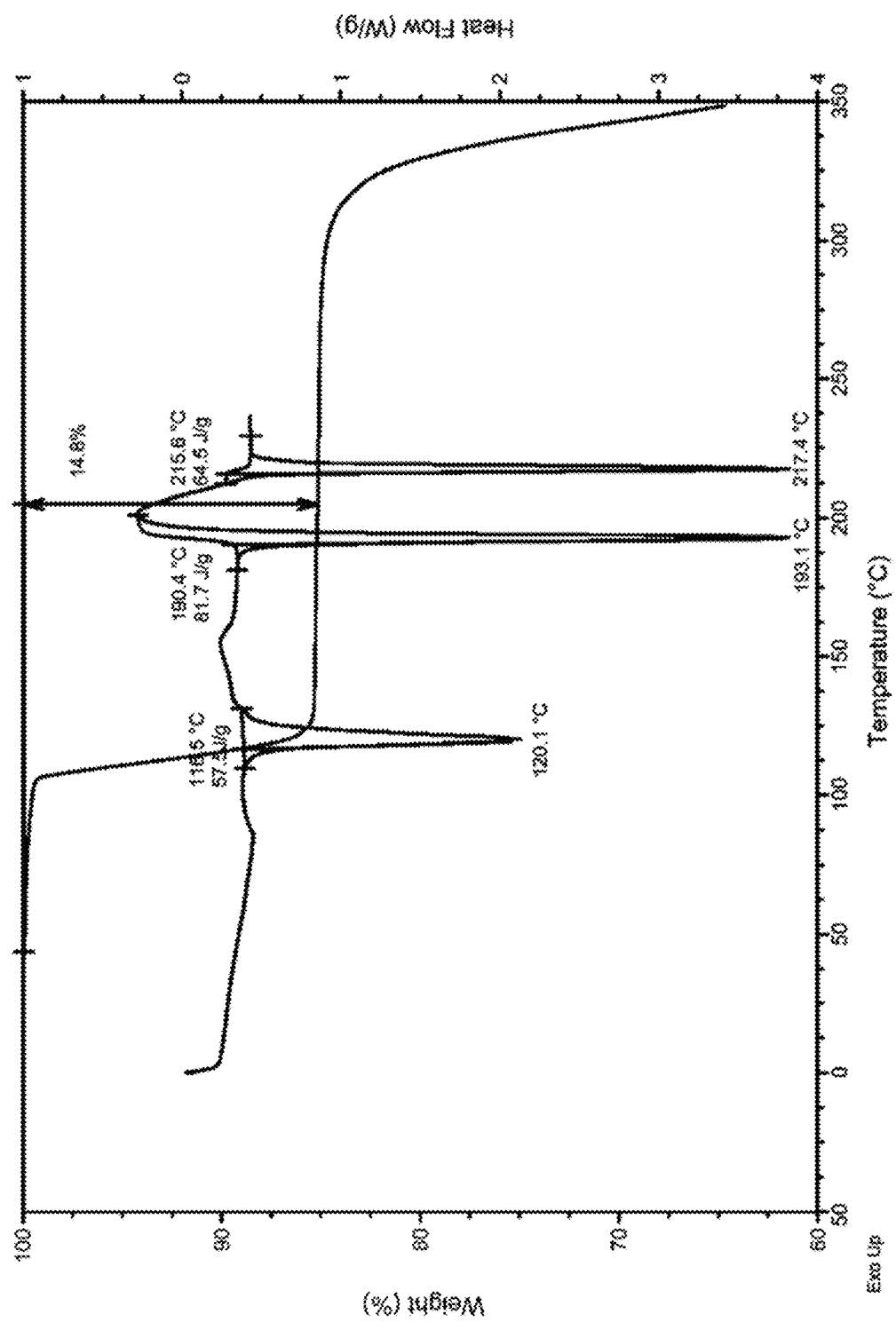
FIG. 13B shows Thermal analysis of GDC-0077 THE solvate
Figure 13C:
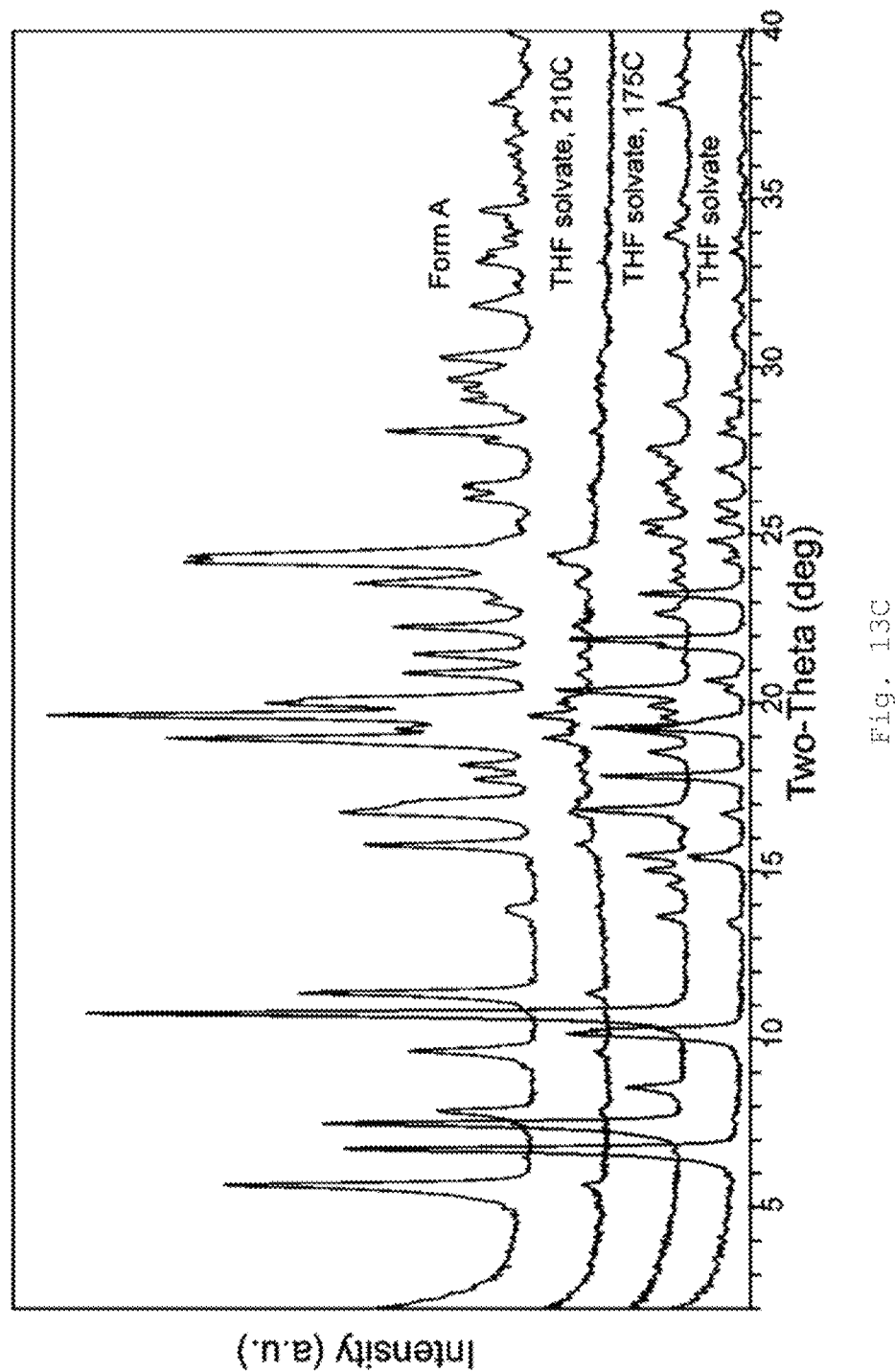
FIG. 13C shows overlay of the XRPD patterns of THE solvate (RT), heated to 175 and 210° C. and Form A. The solvate desolvates to intermediate anhydrous Form which ultimately converts to Form A
Figure 14:
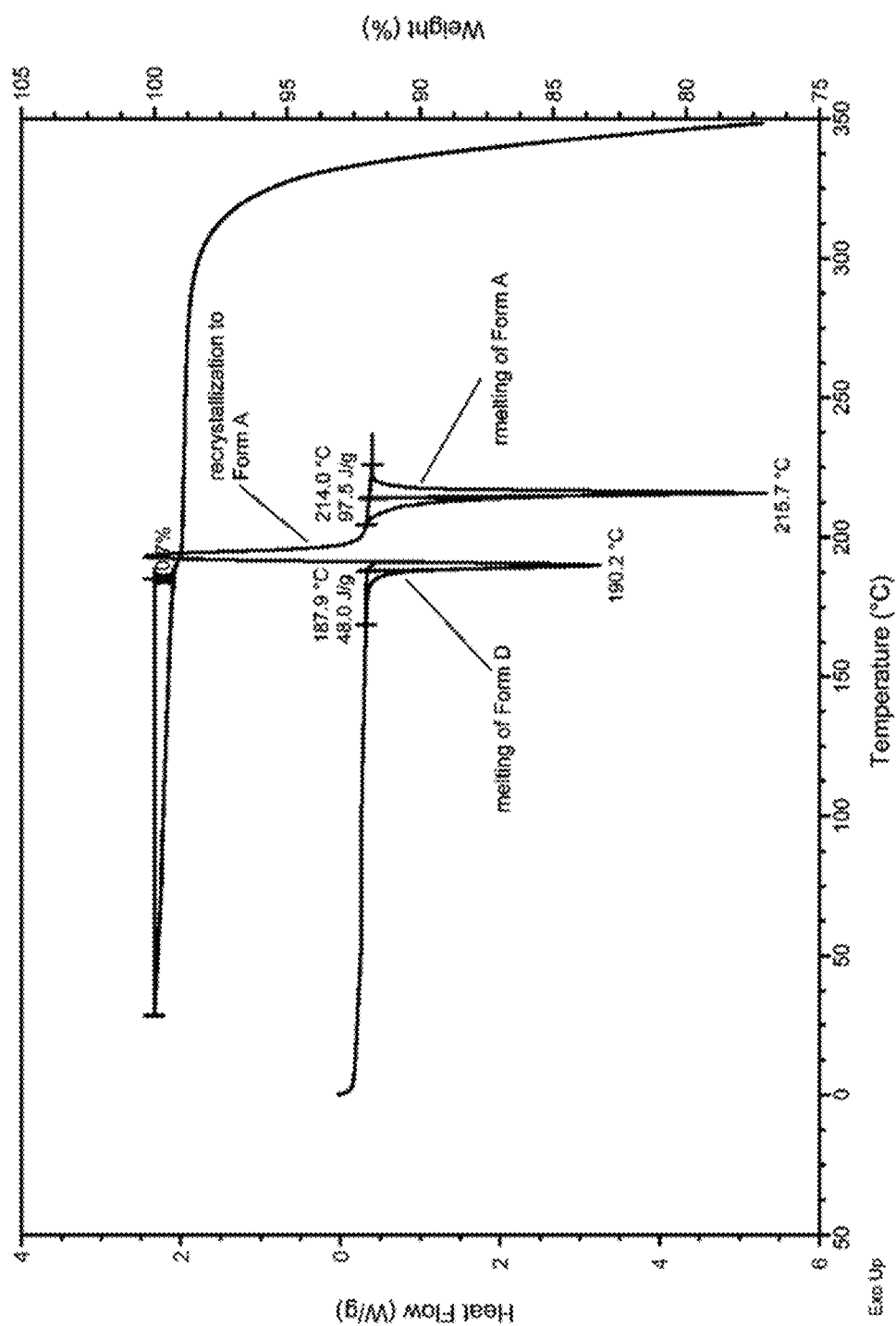
FIG. 14 shows Thermal analysis of Form D, a second anhydrous form obtained by desolvating THE solvate (polymorph of Form A). The phase transitions are marked against the respective endotherms.
Figure 15A:
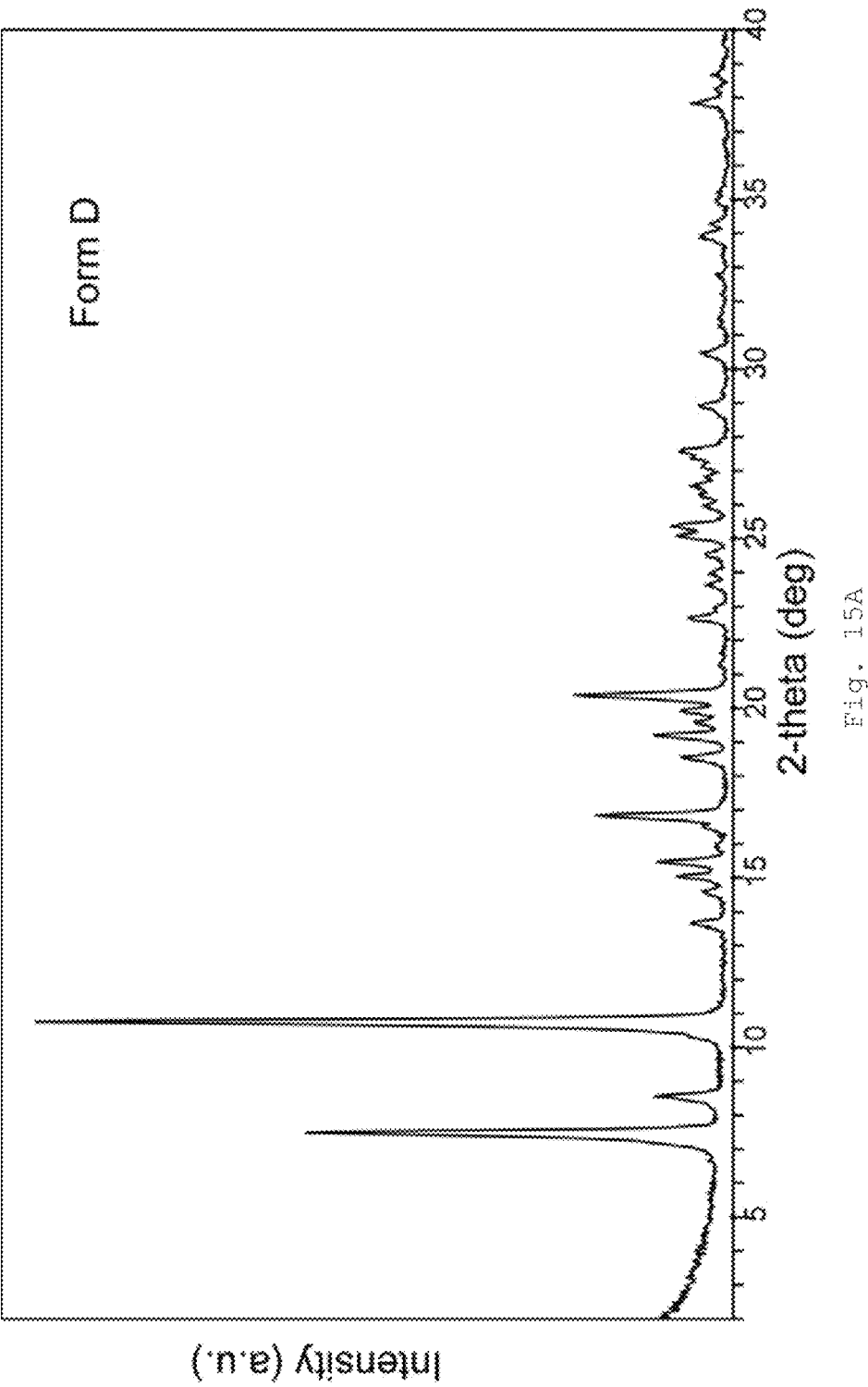
FIG. 15A shows XRPD of anhydrous Form D GDC-0077.

FIG. 13A shows the XRPD pattern of GDC-0077 THF solvate, which was found to contain 10% w/w THF as analyzed by LC-MS. A 14% w/w weight loss was observed by TGA. DSC showed multiple transitions which were further investigated by heating the sample to 175° C. and 201° C., prior to the occurrence of the endotherms (FIG. 13B). An overlay of the XRPD patterns of THF solvate, and the product phases obtained upon heating to 175 and 210° C. shows the solvate desolvates to intermediate anhydrous Form which ultimately converts to Form A (FIG. 13C). At 175° C. and as evident from TGA, THF solvate desolvates completely to form an intermediate anhydrous form (Form D) which subsequently melts and recrystallizes to Form A that melts at 215° C. (onset). The DSC and TGA traces of anhydrous Form D, a second anhydrous form obtained by desolvating THF solvate (polymorph of Form A), are shown in FIG. 14. FIG. 14 shows Thermal analysis of Form D. The phase transitions are marked against the respective endotherms. Negligible weight loss (<1% w/w) prior to melting confirms that Form D is anhydrous. As indicated by DSC, this anhydrous form melts at ~188° C., recrystallizes to Form A which subsequently melts at 215° C. Form D is also obtained by slurrying the crude starting GDC-077, as the Active Pharmaceutical Ingredient (API), in n-propanol:water (99:1 v/v). The THF solvate was found to desolvate to anhydrous Form D. Form D and Form A are monotropically related, with Form A being the thermodynamically stable form over the temperature range studied. FIG. 15A shows XRPD of anhydrous Form D GDC-0077. Table 3 shows the representative XRPD peaks of Form D.

TABLE 3

XRPD Peak Search Report for GDC-0077 Form D

| 2-Theta | d(Å) | BG | Height | H % |
|---|---|---|---|---|
| 7.481 | 11.8070 | 107 | 2400 | 59.5 |
| 8.560 | 10.3211 | 92 | 370 | 9.2 |
| 10.760 | 8.2155 | 70 | 4031 | 100.0 |
| 16.837 | 5.2615 | 44 | 760 | 18.8 |
| 19.198 | 4.6194 | 63 | 401 | 10.0 |
| 20.392 | 4.3516 | 55 | 875 | 21.7 |

Figure 15B:
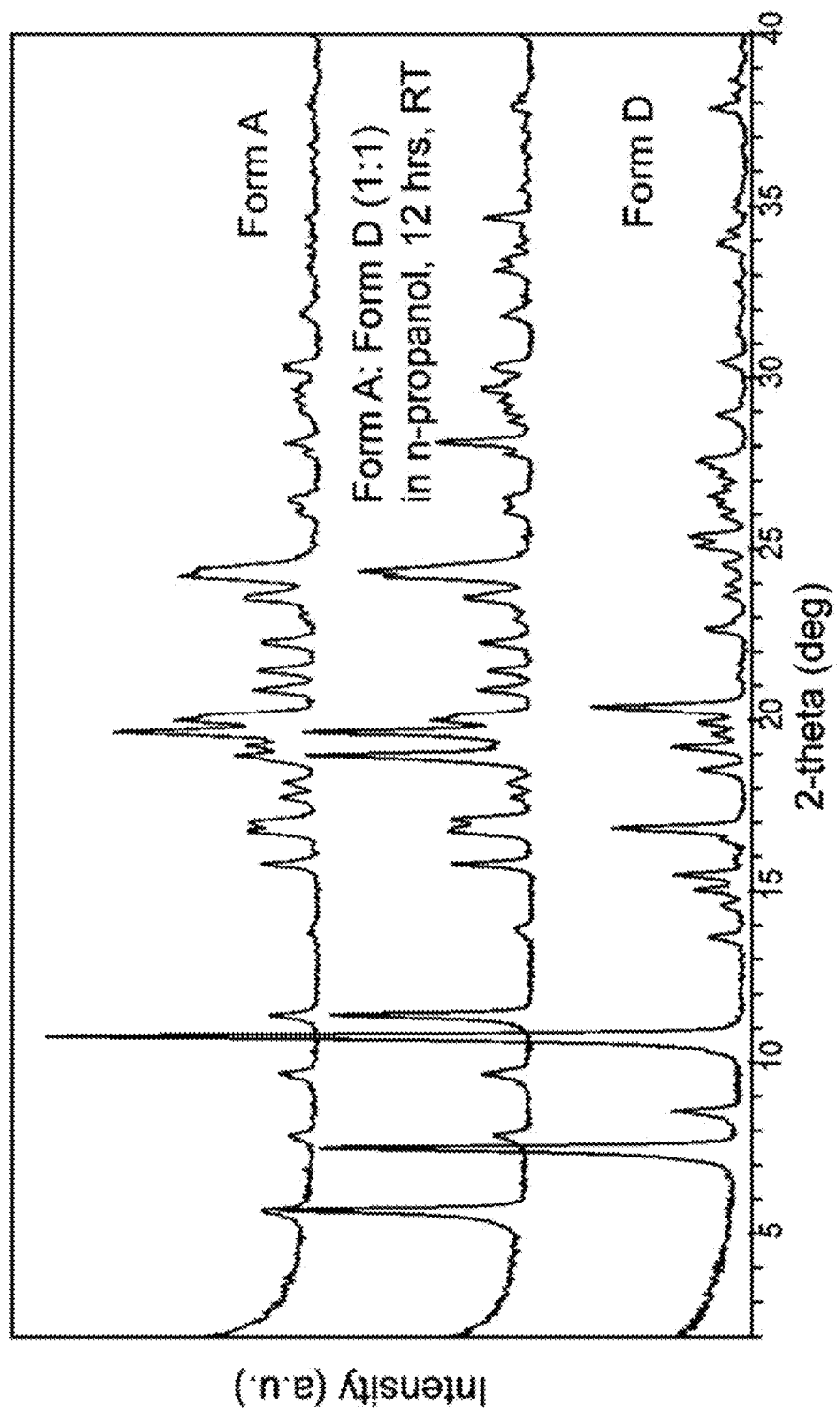
FIG. 15B shows overlay of the XRPD patterns of Forms A, D and final solid form of GDC-0077 obtained after slurrying Forms A and D (1:1 mixture) overnight in n-propanol (RT). Form D converts to Form A in the slurry.

Based on Burger and Ramberger's "Heat of Fusion Rule" of polymorphism, two polymorphs are considered to be monotropic if the one with the higher melting point has a greater heat of fusion as well (Burger and Ramberger, Mikrochimica Acta (1979), 256). In this case, Form A which melts at ~213-215° C. has a heat of fusion of ~100 J/g (FIG. 6A) whereas Form D shows a melting onset of 190° C. with a heat of fusion of ~82-48 J/g (FIG. 14) by thermal analysis of the GDC-0077 THF solvate, depending on the sample history and purity. Although the ΔH (change in enthalpy of fusion, or heat of fusion) for Form D could not be determined accurately, the values provide a good approximation to rule, suggesting that the two forms may be monotropically related. To confirm this further, a slurry bridging experiment was conducted at RT in n-propanol, which had previously yielded Form D from the crude API. FIG. 15B shows overlay of the XRPD patterns of Forms A, D and final solid form of GDC-0077 obtained after slurrying Forms A and D (1:1 mixture) overnight in n-propanol (RT). Form D converts to Form A in the slurry. FIG. 15B shows the XRPD pattern of the solid form isolated from the slurry post 12 hrs of agitation, which matches that of Form A. This confirms that Form D converts to Form A. In other words, Form A is the more stable form between RT to 214° C.

Figure 7A:
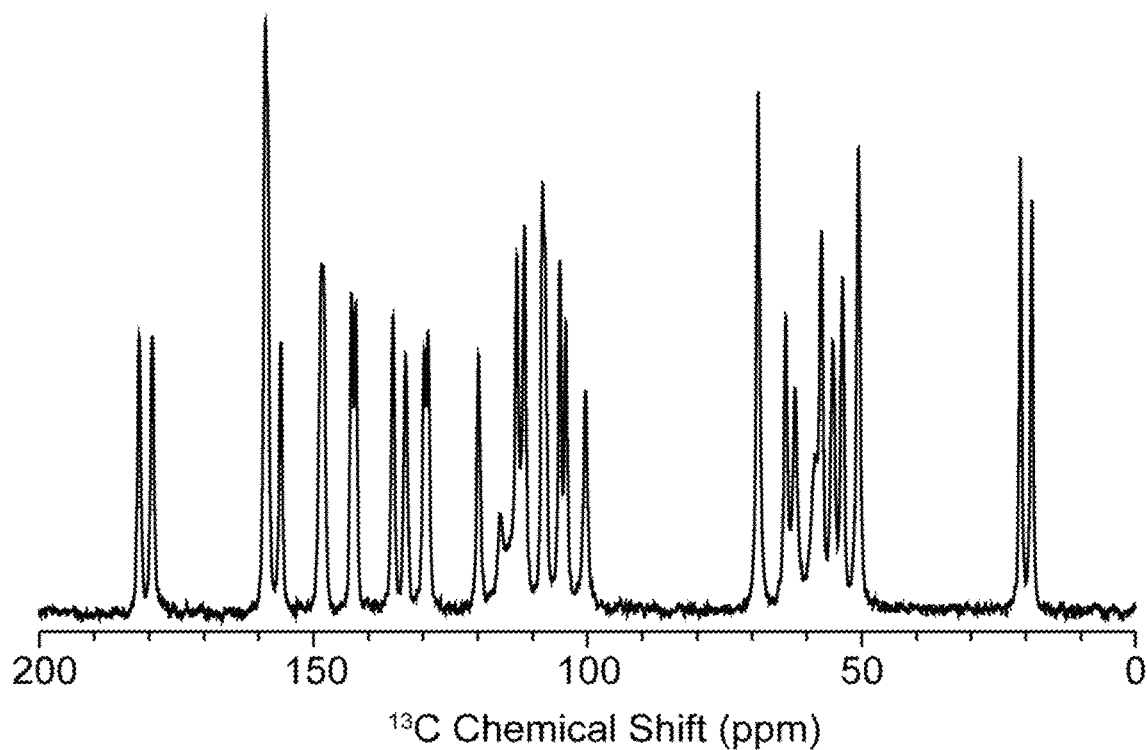
FIG. 7A shows 13C SSNMR (solid-state nuclear magnetic resonance) spectra of anhydrous Form I (Form A) GDC-0077.
Figure 7B:
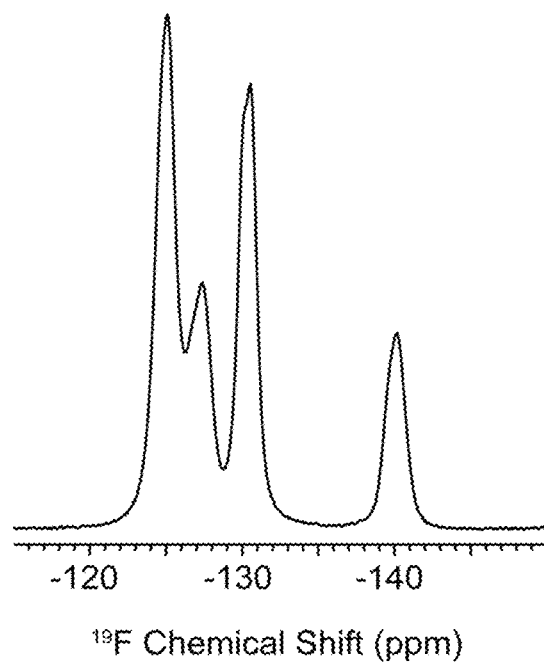
FIG. 7B shows 19F SSNMR of anhydrous Form I (Form A) GDC-0077.
Figure 8:
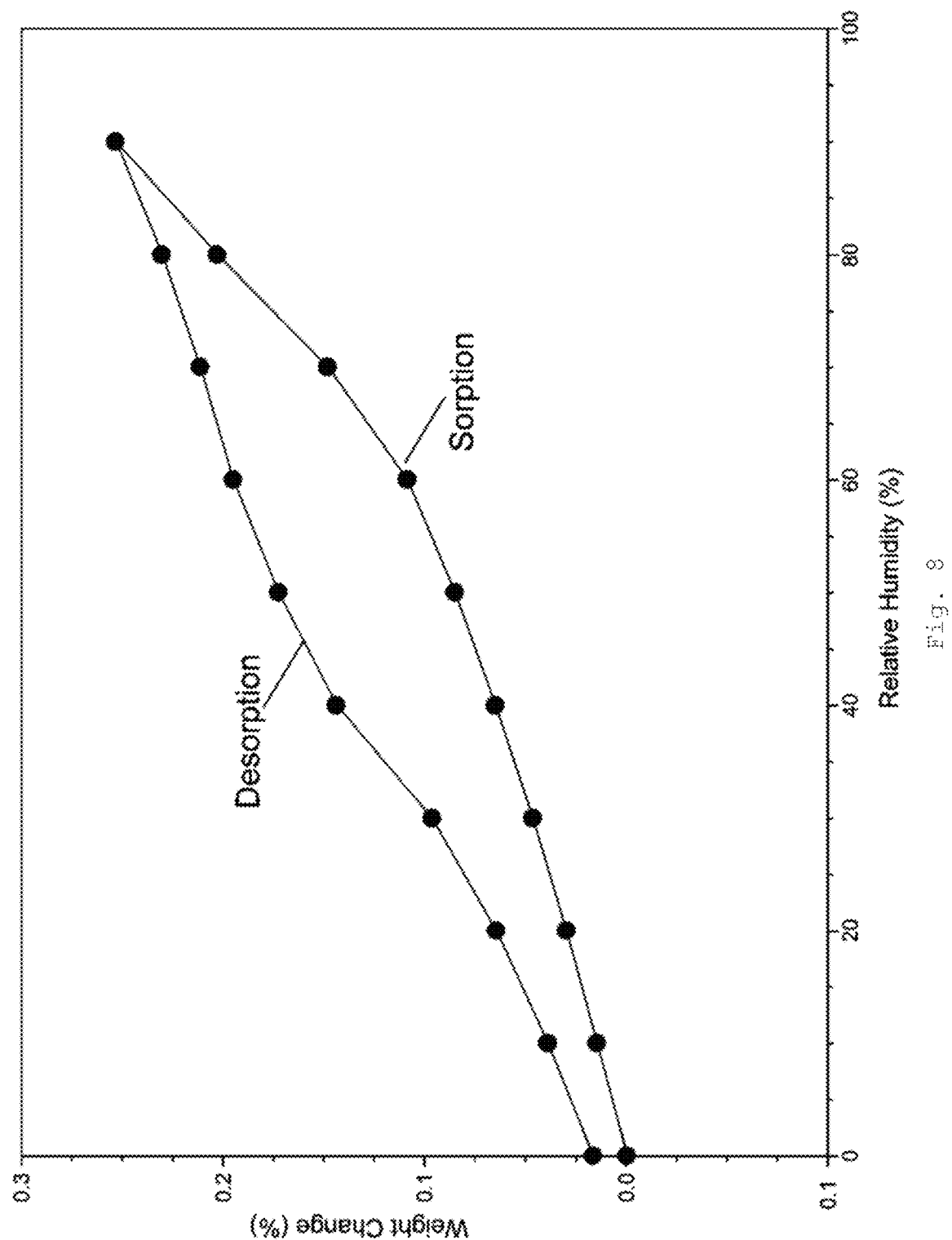
FIG. 8 shows Water sorption behavior of anhydrous Form I (Form A) GDC-0077.
Figure 17:
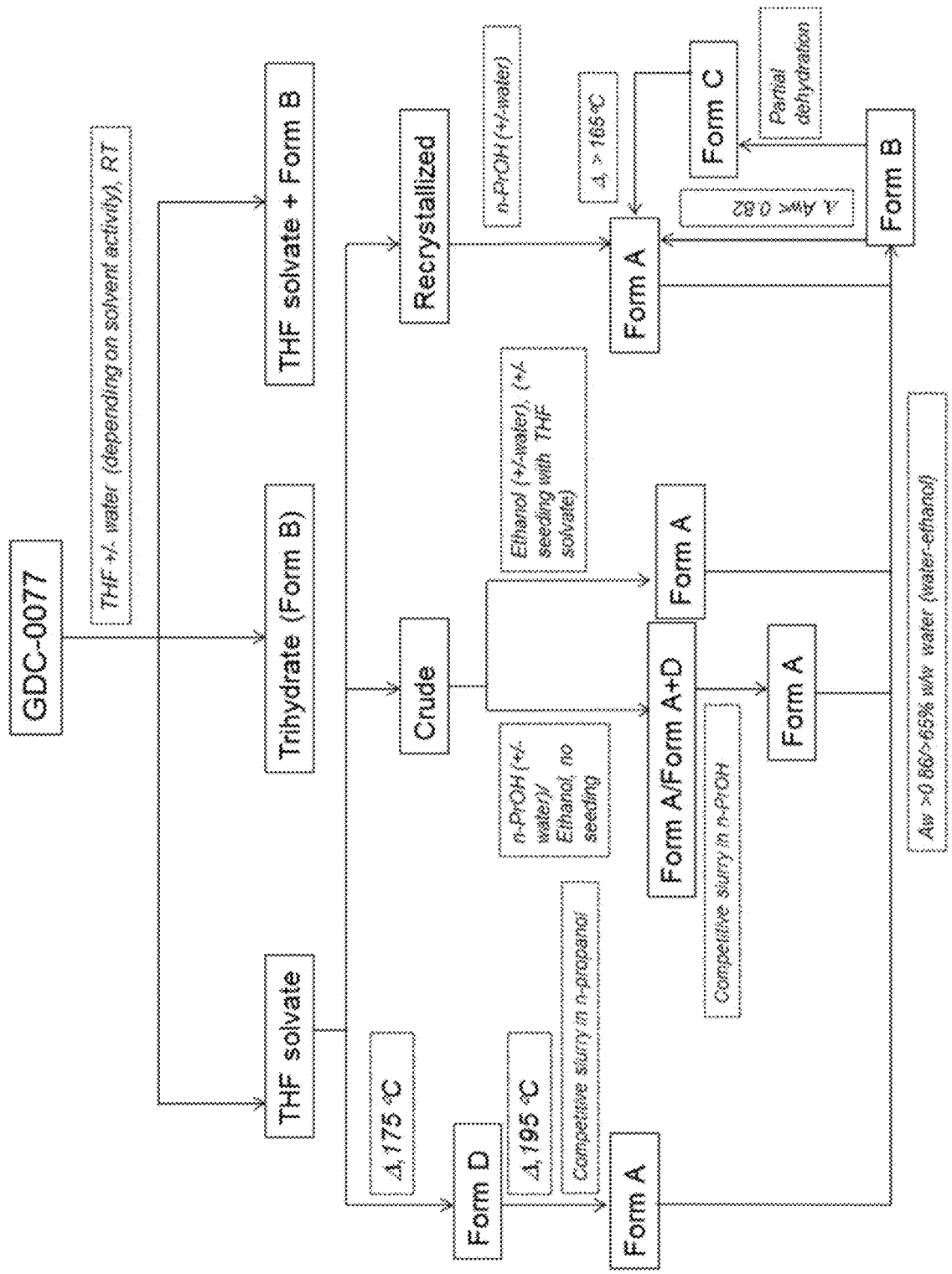
FIG. 17 shows the Solid form landscape for GDC-0077.

FIG. 17 shows the Solid form landscape for GDC-0077, and provides a comprehensive snapshot of the different solid forms identified via high throughput screening and during crystallization optimization. The form landscape, as shown in the Figure, shows the phase transformation between the different forms and details the experimental conditions enabling these transformations as a guide for crystallization and scale up of the appropriate form. XRPD (FIG. 4) and solid-state NMR (FIGS. 7A and 7B confirmed Form A. FIG. 7A shows 13C SSNMR (solid-state nuclear magnetic resonance) spectra of anhydrous Form I (Form A) GDC-0077. FIG. 7B shows 19F SSNMR of anhydrous Form I (Form A) GDC-0077. Thermal analysis DSC and TGA traces are included in FIG. 6. Based on negligible weight loss and absence of any dehydration event prior to melting at 212° C., Form A is confirmed to be anhydrous. Microscopy data (SEM and PLM) are shown in FIGS. 5A and 5B, where the GDC-0077 Form API particles appear to be plate like. Table 4 shows the Particle Size Distribution (PSD) data for 5, 15 and 30 second sonication. Water sorption data of anhydrous Form I (Form A) GDC-0077 is shown in FIG. 8. The compound absorbs negligible moisture (0.25% w/w) up to 90% RH (25° C.).

TABLE 4

Particle Size Distribution (PSD) for GDC-0077 Form A as a function of sonication time.

| Sample | D10 (µm) | D50 (µm) | D90 (µm) | D[4,3] (µm) |
|---|---|---|---|---|
| GDC-0077 Form A | 4.76 | 27.73 | 208.16 | 74.60 |
| 5 sec sonication | 3.24 | 14.87 | 40.92 | 19.09 |
| 15 sec sonication | 2.70 | 10.93 | 27.59 | 13.44 |

Effect of Size Reduction on Form A

Milling of Form A may optimize certain PK properties. A scaled up Form A lot was milled and also placed on stability studies (40° C./75% RH, 25° C./60% RH, open vials). Three more lots were also milled which behaved similarly upon milling. A milled representative lot was characterized and the physical form was determined. This lot was slurried in 100% ethanol to obtain Form A and milled using a jet mill at for 3.5 hrs with 60 psi pressure. The yield was found to be 91%. The particle size analysis (PSD) was determined to be D10=0.7 µm, D50=2.7 µm, D90=6.7 µm. Post milling, a portion of the API (Active Pharmaceutical Ingredient, i.e. GDC-0077) batch was placed on stability at 40° C./75% RH and 25° C./60% RH in open vials. Solid-state data was collected at 4 and 8 weeks to evaluate effect of temperature and humidity on the physical form. The milled and stability samples were characterized by XRPD, PLM, DSC, TGA, Water sorption analysis and surface area analysis. DSC runs were performed in the modulated mode using non-hermetically crimped pans, a heating rate of 1° C./min from 0-175° C., modulation amplitude of ±1° C. and a period of 60 seconds.

Figure 16A:
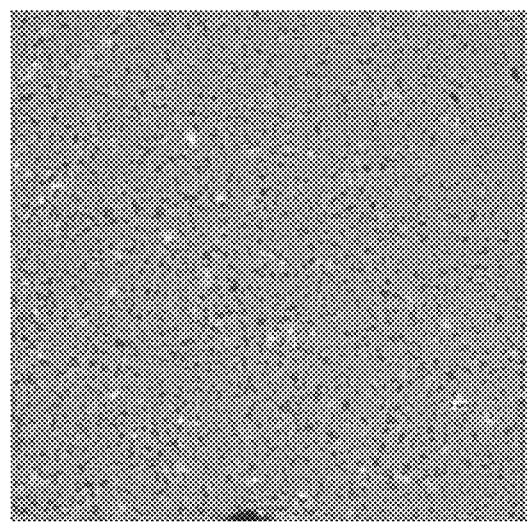
FIG. 16A shows PLM of milled GDC-0077. Form A remains stable upon milling.
Figure 16B:
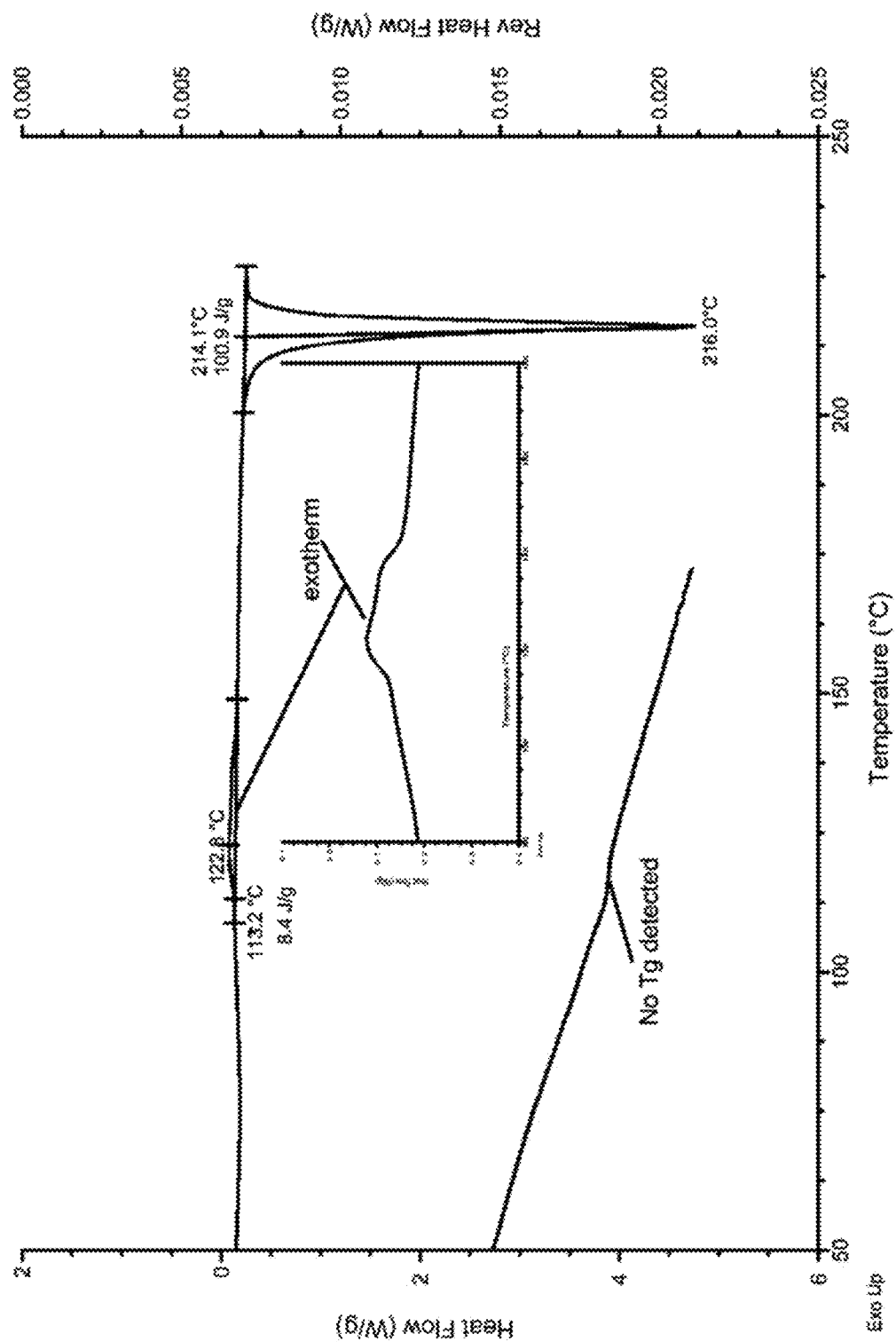
FIG. 16B shows DSC and MDSC traces of GDC-0077 milled lot. Milling induces disorder which is evidenced by the emergence of an exotherm (marked in inset at 113° C.) that indicated recrystallization of the disordered phase and subsequent melting of Form A (endotherm at 214° C.). MDSC does not reveal a Tg near the exotherm.

To characterize the effects of milling via XRPD, thermal analysis and water sorption showed the form remains unchanged upon milling but baseline counts appear to have undergone an increase along with decrease in peak resolution. The PLM image (FIG. 16A) shows the crystallites to be of uniform size and of the order of about 5 µm, which corroborates the PSD data, and demonstrates the milled GDC-0077 Form A remains stable upon milling. The indication of generation of disorder is more obvious in the DSC trace where a small exotherm is observed at 113° C. (inset of FIG. 16B) followed by the melting endotherm of Form A at 214° C. (FIG. 16B). This endotherm may be attributed to disorder, which is most likely on the surface, as is the case with milled materials. MDSC (Modulated Differential Scanning Calorimetry) did not reveal a glass transition temperature (Tg), but the mere absence of a Tg does not rule out the possibility of surface amorphization since the highly mobile, disordered surface tend to crystallize almost instantaneously at Tg. The weight loss, prior to melting is higher for the milled material in comparison to the unmilled lot, owing to generation of disorder as measured by thermogravimetry (TGA). Milling generates a marked increase (OX) in surface area from 0.78 to 6.68 µm2/g upon milling (Table 5). This surface area determined by BET analysis, was found to be twice that generated simply by taking into account the sauter mean diameter (D3,2) fluid dynamics method of defining particle size, which was 3.42 µm2/g. This indicates that the marked increase in surface area is contributed by generation of surface disorder. In addition, a 1% w/w increase in moisture uptake is observed in the water sorption profile of the milled lot when compared to the unmilled material (weight gain of 0.25% up to 90% RH, FIG. 8), which further confirms presence of disorder upon milling.

TABLE 5

Surface area of milled and unmilled GDC-0077.

| GDC-0077 | BET Surface Area (m2/g) |
|---|---|
| Unmilled | 0.78 ± 0.03 |
| Jet Milled | 6.68 ± 0.16 |

XRPD, DSC and TGA patterns of milled samples at T0, 4 and 8 weeks, time points show the GDC-0077 physical form remains unchanged under stress-stability conditions (open vials) as evident from XRPD. Reduction or disappearance of milling induced disorder upon exposure to moisture is evident from the decrease in ΔH (25° C./60% RH) or complete absence of the recrystallization endotherm (40° C./75% RH) in the stability samples by DSC. This is not unexpected since annealing or recrystallization of a disordered phase may occur upon exposure to moisture which acts as a plasticizer. Thus, GDC-0077 Form A shows milling induced disorder, but the crystalline form remains unchanged upon size reduction. The disorder is speculated to be surface related and reduced/anneals to crystalline form upon exposure to moisture. The physical form remains stable under open conditions up to 8 weeks at 40° C./75% RH and 25° C./60% RH.

Methods of Treatment

Crystalline forms of GDC-0077 detailed herein are useful for treating a human or animal patient suffering from a disease or disorder arising from abnormal cell growth, function or behavior associated with PI3K such as cancer, may thus be treated by a method comprising the administration thereto of a crystalline polymorph of GDC-0077 detailed herein (e.g., crystalline anhydrate Form A, crystalline anhydrate Form D, or crystalline trihydrate Form B). A human or animal patient suffering from cancer may also be treated by a method comprising the administration thereto of a crystalline polymorph of GDC-0077 detailed herein. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

Based on expression analysis, immunohistochemical analysis and on cell line profiling, malignancies of the colon, breast, cervix, stomach, lung, and multiple myeloma are most likely to respond to PI3K modulators or inhibitors.

Combination Therapy

Polymorphs of GDC-0077 may be employed alone or in combination with additional therapeutic agents for the treatment of a disease or disorder described herein, such as inflammation or a hyperproliferative disorder (e.g., cancer). In certain embodiments, a crystalline polymorph of GDC-0077 detailed herein (e.g., crystalline anhydrate Form A, crystalline anhydrate Form D, or crystalline trihydrate Form B) is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a CDK4/6 inhibitor, Bcl-2 inhibitor, a JAK inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to GDC-0077 such that they do not adversely affect each other. Such compounds are suitably present in combination in amounts that are effective for the purpose intended. In one embodiment, a composition of this invention comprises a crystalline polymorph of GDC-0077 detailed herein (e.g., crystalline anhydrate Form A, crystalline anhydrate Form D, or crystalline trihydrate Form B), in combination with a therapeutic agent such as a CDK4/6 inhibitor.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combinpation therapy, effective dosages of two or more active ingredients are administered together.

In a particular embodiment of therapy, a crystalline polymorph of GDC-0077 detailed herein (e.g., crystalline anhydrate Form A, crystalline anhydrate Form D, or crystalline trihydrate Form B), may be combined with other therapeutic, hormonal or antibody agents such as those described herein, as well as combined with surgical therapy and radiotherapy. Combination therapies according to the present invention thus comprise the administration of a crystalline polymorph of GDC-0077 detailed herein (e.g., crystalline anhydrate Form A, crystalline anhydrate Form D, or crystalline trihydrate Form B), and the use of at least one other cancer treatment method. The amounts of the crystalline polymorph of GDC-0077 and the other pharmaceutically active therapeutic agent(s) and the relative timings of administration will be selected in order to achieve the desired combined therapeutic effect.

Additional therapeutic agents employed in combination with a crystalline polymorph of GDC-0077 detailed herein (e.g., crystalline anhydrate Form A, crystalline anhydrate Form D, or crystalline trihydrate Form B), include 5-FU, docetaxel, eribulin, gemcitabine, cobimetinib, ipatasertib, paclitaxel, tamoxifen, fulvestrant, GDC-0810, dexamethasone, palbociclib, bevacizumab, pertuzumab, trastuzumab emtansine, trastuzumab and letrozole.

In some embodiments, provided is a method for treating cancer in a subject in need thereof comprising administering to the subject a therapeutically effective amount of a crystalline polymorph of GDC-0077 detailed herein (e.g., crystalline anhydrate Form A, crystalline anhydrate Form D, or crystalline trihydrate Form B). In some embodiments, the cancer is a breast cancer. In some embodiments, the cancer is a hormone receptor positive (HR+) breast cancer. In some embodiments, the cancer is an estrogen receptor positive (ER+) breast cancer. In some embodiments, the cancer is a HER2-negative breast cancer. In some embodiments, the cancer is a HR+ metastatic breast cancer. In some embodiments, the cancer is a HR-positive, HER2-negative advanced breast cancer. In some embodiments, the cancer is a HER2-negative, ER-negative and progesterone receptor (PR)-negative breast cancer. In some embodiments, the subject is human. In some embodiments, the subject is a postmenopausal woman. In some embodiments, the breast cancer subtype is Basal or Luminal. In some embodiments, the cancer has a PIK3CA mutation. In some embodiments, the cancer expresses a PIK3CA mutant selected from E542K, E545K, Q546R, H1047L and H1047R. In some embodiments, the cancer expresses a PTEN mutant.

In some of these embodiments, the method of treating cancer (e.g., breast cancer) further comprising administering to the subject one or more additional therapeutic agent(s). In some embodiments, the one or more additional therapeutic agent(s) is/are selected from a CDK4/6 inhibitor (e.g., palbociclib, ribociclib and abemaciclib), a selective estrogen receptor degrader (SERD) (e.g., fulvestrant), and an aromatase inhibitor (e.g., letrozole). In some embodiments, the additional therapeutic agent palbociclib. In some embodiments, the additional therapeutic agent is fulvestrant. In some embodiments, the one or more additional therapeutic agents are palbociclib and letrozole.

An aspect of the invention is a crystalline polymorph of GDC-0077 detailed herein (e.g., crystalline anhydrate Form A, crystalline anhydrate Form D, or crystalline trihydrate Form B), or a pharmaceutical composition comprising a crystalline polymorph of GDC-0077 detailed herein (e.g., crystalline anhydrate Form A, crystalline anhydrate Form D, or crystalline trihydrate Form B), for use in the treatment of cancer. In some embodiment the cancer is a HR-positive and HER2-negative breast cancel expressing a PIK3CA mutation. In some embodiments, the polymorphs for use further comprise one or more additional therapeutic agents (e.g., fulvestrant, palbociclib and/or letrozole).

An aspect of the invention is the use of a crystalline polymorph of GDC-0077 detailed herein (e.g., crystalline anhydrate Form A, crystalline anhydrate Form D, or crystalline trihydrate Form B), or a pharmaceutical composition comprising a crystalline polymorph of GDC-0077 detailed herein (e.g., crystalline anhydrate Form A, crystalline anhydrate Form D, or crystalline trihydrate Form B), in the manufacture of a medicament for use in the treatment of cancer. In some embodiment the cancer is a HR-positive and HER2-negative breast cancel expressing a PIK3CA mutation. In some embodiments, the uses further comprise one or more additional therapeutic agents (e.g., fulvestrant, palbociclib and/or letrozole).

Pharmaceutical Compositions and Formulations

A polymorph form of GDC-0077, Formula I, may be formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0077 in association with one or more pharmaceutically acceptable carrier, glidant, diluent, or excipient.

Suitable carriers, diluents, glidants, and excipients are well known to those skilled in the art and include materials such as carbohydrates, waxes, water soluble and/or swellable polymers, hydrophilic or hydrophobic materials, gelatin, oils, solvents, water and the like.

The formulations may be prepared using conventional dissolution and mixing procedures. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of a polymorph form of GDC-0077 may be prepared for various routes and types of administration with pharmaceutically acceptable diluents, carriers, excipients, glidants or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a tablet, a pill, a capsule, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as lactose, sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa. Other examples of drug formulations can be found in Liberman, H. A. and Lachman, L., Eds., Pharmaceutical Dosage Forms, Marcel Decker, Vol 3, $2^{nd}$ Ed., New York, N.Y.

Tablets may comprise one or more pharmaceutically acceptable carrier, glidant, diluent, or excipient selected from microcrystalline cellulose, lactose, sodium starch glycolate, and magnesium stearate.

Pharmaceutically acceptable glidants may be selected from silicon dioxide, powdered cellulose, microcrystalline cellulose, metallic stearates, sodium aluminosilicate, sodium benzoate, calcium carbonate, calcium silicate, corn starch, magnesium carbonate, asbestos free talc, stearowet C, starch, starch 1500, magnesium lauryl sulfate, magnesium oxide, and combinations thereof.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences 18$^{th}$ Ed. (1995) Mack Publishing Co., Easton, Pa. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

Administration of Pharmaceutical Compositions

The pharmaceutical compositions of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 1 mg to about 100 mg of a polymorph form of GDC-0077, such as about 2 mg to about 50 mg, about 3 mg to about 20 mg, about 3 mg to about 15 mg, about 3 mg to about 20 mg, about 1 mg, about 2 mg, about 3 mg, about 4 mg, about 5 mg, about 6 mg, about 9 mg, about 12 mg, about 15 mg, or about 20 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

EXAMPLES

Example 1 Isolation and Physicochemical Characteristics of (S)-2-((2-((S)-4-(Difluoromethyl)-2-oxooxazolidin-3-yl)-5,6-dihydrobenzo[f]imidazo[1,2-d][1,4]oxazepin-9-yl)amino)propanamide, GDC-0077

GDC-0077 was prepared according to WO 2017/001645, US 2017/0015678, each of which are incorporated by reference.

(S)-3-(9-Bromo-5,6-dihydrobenzo[f]imidazo[1,2-d][1,4] oxazepin-2-yl)-4-(difluoromethyl)oxazolidin-2-one (600 mg, 1.50 mmol), L-alanine (267 mg, 3.00 mmol), cuprous iodide (57 mg, 0.30 mmol) and potassium phosphate tribasic (637 mg, 3.00 mmol) were suspended in dimethyl sulfoxide (6.0 mL). The reaction mixture was heated at 100° C. for 2 hours. Upon allowing to cool to room temperature, dimethyl sulfoxide (4.0 mL), ammonium chloride (480 mg, 9.00 mmol), and triethylamine (3.1 mL, 22.5 mmol) were added. To the resultant stirred suspension was added, 1-[bis(dimethylamino)methylene]-1H-1,2,3-triazolo[4,5-b]pyridinium 3-oxide hexafluorophosphate (5.10 g, 13.5 mmol), portionwise over 5 minutes. The reaction mixture was stirred at room temperature for 1 hour and then filtered through Celite®, washing with ethyl acetate. The organic extracts were washed with saturated aqueous sodium bicarbonate and the aqueous phase was extracted with ethyl acetate. The combined organic extracts were washed with brine, dried over sodium sulfate, filtered and evaporated in vacuo. The crude residue was purified via flash chromatography on silica gel (solvent gradient: 0-5% methanol in dichloromethane) and then by chiral supercritical fluid chromatography to yield 294 mg (46%) of GDC-0077 as an off-white solid. LCMS (ESI): $R_T$ (min)=2.89 [M+H]$^+$=408, Method=A; $^1$H NMR (400 MHz, DMSO-d$_6$) δ 8.00 (d, J=8.7 Hz, 1H), 7.38 (br s, 1H), 7.18 (s, 1H), 7.00 (br s, 1H), 6.71 (t, J=55.9 Hz, 1H), 6.41 (dd, J=8.8, 2.3 Hz, 1H), 6.16 (d, J=7.2 Hz, 1H), 6.09 (d, J=1.9 Hz, 1H), 5.02-4.89 (m, 1H), 4.63-4.52 (m, 2H), 4.39-4.30 (m, 4H), 3.76 (quintet, J=7.0 Hz, 1H), 1.30 (d, J=7.1 Hz, 3H).

GDC-0077 Form A (anhydrate) was obtained by slurring GDC-0077 in ethanol at 50° C. for 4 hours and then evaporating the solvent under nitrogen purge to give the highly crystalline Form A. DSC thermogram showed one endothermic transition with an onset at ~212-214° C. with an associated heat of fusion of ~107 J/g. Water solubility of Form A at room temperature is 30.8 µg/mL at a pH of 7.06. The trihydrate form was obtained by slurrying Form A in DI water over 4 days (RT), centrifuging the slurry to remove supernatant and then drying the solid at RT for a few hours.

Dry granulation of Form A GDC-0077 using a roller compactor was followed by a tableting operation. Additional ingredients in the tablets included microcrystalline cellulose (Avicel® PH 102, FMC BioPolymer), lactose (FastFlo®

316, Foremost Farms USA), sodium starch glycolate (EX-PLOTAB, JRS Pharma), and magnesium stearate (Hyqual®, Macron Fine Chemicals).

Example 2 High Throughput Polymorph Screening (HTS)

96-Well plate automated HTS using the Symyx CM2 system (Freeslate Inc., CA) was conducted to identify potential polymorphic forms for GDC-0077. Approximately 20 mg of API was added to each well, to which 800 µl (microliters) of solvent (neat or mixture) was added and the slurry was stirred for 2 hours at 50° C. Solvents included water, 1,2-dichloroethane, heptane, cyclohexane, ethanol, 1-propanol, acetonitrile, butylamine, nitromethane, 1,4-dioxane, benzene, perfluoroheptane, ethyl acetate, (trifluoromethyl)benzene, butan-2-one (MEK), 1,2-dimethoxyethane, 2-methyltetrahydrofuran, carbon tetrachloride, dimethylacetamide, tetrahydrofuran (THF), acetone, anisole, toluene, and 2-ethoxyethanol. From this "master" plate, the supernatant was filtered and distributed to three separate plates for evaporation, precipitation by anti-solvent addition and controlled cooling over 8-10 hrs from 50-20° C. Details on solvents as well as anti-solvents are outlined in FIG. 2. In all cases residual solvents were either evaporated or siphoned off, and the solid was examined using polarized light microscopy and X-ray powder diffractometry. XRPD patterns of crystalline hits were compared followed by scale up of the potentially "different" hits and their characterization.

Example 3 Slurry Bridging

Deionized (DI) Water-ethanol (absolute alcohol) mixtures of different compositions ranging from 0-100% water were prepared and their water activities were measured using a water activity meter. Slurry experiments were set up at RT wherein 1:1 mixtures of trihydrate and anhydrous forms of GDC-0077 (40 mg total) were added to these solvent mixtures (1.5 mL liquid) and agitated at RT over 4 days. After 4 days, the samples were aliquoted and centrifuged. The solids were analyzed by XRPD and the supernatant was analyzed for water activity. 1:1 mixture of Forms A and D was slurried in in-propanol overnight at RT. The slurry was centrifuged and the solid form was analyzed by XRPD.

Example 4 Ambient X-ray Powder Diffractometry (XRPD)

XRPD patterns were collected with a Rigaku SmartLab® diffractometer (Rigaku Corp., Tokyo, Japan), using an incident beam of Cu Kα (1.541904 Å) radiation generated using Cross Beam optics (40 kV×44 mA). GDC-0077 powder samples were packed using the top fill method onto zero-background holders and scans were acquired at a scan speed of 1 or 3.0°/min and step size of 0.02 or 0.04° 2θ (2-theta) over 2-40° 2θ range in the bragg-brentano or parallel beam configuration (reflection geometry). Data was analyzed using commercial software (JADE®, version 9, Materials Data Inc., Livermore, Calif.).

Example 5 Water Sorption Analysis

About 5-6 mg of powder sample was placed in the sample pan of an automated water sorption analyzer (Q5000SA, TA instruments, New Castle, Del.) at 25° C. and a nitrogen flow rate of 200 mL/min. The sample was initially "dried" at 0% RH for a total of 600 minutes (at 60 followed by 25° C.), following which it was subjected to progressive increase in RH from 0-90%, in increments of 10% with a dwell time of 240 minutes at every RH with a dm/dt window of 0.001% for 30 minutes. This was followed by a progressive decrease in RH in decrements of 10% back to 0% RH, using the same protocol. For hydrate samples, the process was reversed where the starting RH was maintained at 90%, followed by a progressive step-wise lowering to 0%, followed by similar step wise increase back to 90%. This was done to ensure that the water of hydration is retained at the start of the experiment.

Example 6 Water Activity

An Aqualab 4TEV (Decagon Devices, WA) was used as the water activity meter in the capacitance sensor mode to acquire data at 25±0.2° C. for solvent mixtures and slurry supernatants. Instrument was calibrated using vendor provided standards (saturated salt solutions) over the $a_w$ range of 0.25-1. All $a_w$ values are obtained after stabilization of three consecutive reads.

Example 7 Differential Scanning Calorimetry (DSC)

Approximately 3-8 mg of powder sample was analyzed using a DSC Q2000™ (TA instruments, New Castle, Del.) equipped with a refrigerated cooling accessory. Samples were packed in non-hermetically pans (Tzero™, aluminum pans) and typically heated from 20-250° C. under dry nitrogen purge. The instrument was calibrated using sapphire (baseline) and indium (temperature and cell constant). The data was analyzed using commercial software (Universal Analysis 2000, version 4.7 Å, TA Instruments). The experimental conditions and pan configurations are as follows:

Example 8 Thermogravimetry (TGA)

Non-isothermal experiments: In a thermogravimetric analyzer (Discovery TGA, TA instruments), 3-4 mg of GDC-0077 samples were heated in an open aluminum pan from RT to 350° C. at a heating rate of 10° C./min and RT to 350 under dry nitrogen purge. Temperature calibration was performed using Alumel® and Nickel. Standard weights of 100 mg and 1 gm were used for weight calibration.

Isothermal experiments: In a thermogravimetric analyzer (Q500 TGA, TA instruments), 3-4 mg of GDC-0077 samples were heated in an open aluminum pan from RT to 60° C. at a heating rate of 10° C./min held isothermally at 60° C. overnight. Samples were then either analyzed by XRPD or left to equilibrate at RT for 4 hours in the sample pan and then rerun isothermally at 60° C. using the same experimental parameters as mentioned above.

Example 9 Polarized Light Microscopy (PLM)

Samples were dispersed in silicon oil and observed under cross polarizers of a video enhanced Leica DM 4000B microscope equipped with a high resolution CCD camera and motorized stage (Clemex Technologies Inc., Longueuil, Quebec, Canada) at 200× magnification. Photomicrographs were acquired using the Clemex Vision PE software (Clemex Technologies Inc., Longueuil, Quebec, Canada).

Example 10 Scanning Electron Microscopy (SEM)

Powder sample sputter coated on SEM stub and then examined using a benchtop Phenom SEM (Nanoscience Instruments, Inc., AZ). Micrographs were acquired at different magnifications.

Example 11 Particle Size Distribution Analysis (PSD)

Particle size analysis was performed using a Malvern Mastersizer 2000 instrument equipped with a Hydros 2000SM wet dispersion attachment (Malvern Instruments Ltd., Malvern, UK). ~30 mg of API was weighed into a vial and 1 mL of 0.1% Span 85 in heptane was added. The vial was sonicated for 5 seconds, about 0.3 mL was added to the sampler at a stir speed of 1500 rpm, and a PSD was performed at an obscuration of 10-20%. The sample was then sonicated for 10 more seconds (a total of 15 seconds), about 0.3 mL was added to the sampler, a PLM image was acquired, and PSD was performed. The same sample was then sonicated for another 15 seconds (a total of 30 seconds), about 0.3 mL was added, a PLM photo was taken and PSD was performed. From the sonication study, an appropriate sonication period was chosen. The PLM images and PSDs were used to determine how much sonication the sample needed to disperse clumps but prevent or minimize crystal fracturing. Three more samples, of ~10 mg, were weighed into vials and 1 mL of 0.1% Span 85 in heptane was added. The samples were sonicated for the sonication period determined in the sonication study. The final PSD analysis was performed in triplicate using the predetermined sonication period. The instrument was rinsed twice with isopropyl alcohol (IPA) and once with heptane before being filled with 0.1% Span 85 in heptane for each sample. After the last sample had run, the instrument was rinsed with IPA once.

Example 12 Surface Area Analysis

Surface area measurement was conducted using a Micromeritics ASAP 2460 with a Micromeritics Smart VacPrep attachment (Micromeritics Instrument Corp., GA). A sample of 500 mg-1 g was weighed into an empty ASAP 2460 tube and placed on the Smart VacPrep, degassed for 24 hours under ambient conditions and then exposed to Krypton gas adsorption at 25° C. and 100 mm Hg hold pressure. An 11-point measurement was made in the relative pressure range of 0.050-0.300 and the data was analyzed using MicroActive software provided by the vendor.

Example 13 Solid-state Nuclear Magnetic Resonance Spectroscopy (SSNMR)

All 13C (@ 8 kHz spinning speed) SSNMR experiments were conducted using the 500 MHz Bruker instrument (Bruker BioSpin GmbH, Karlsruhe, Germany) 13C data were acquired using a CP/TOSS sequence. 1-2 K scans were collected for signal averaging. A contact time of 4 ms (milliseconds) and a recycle delay of 5 seconds was used. Spinal 64 sequence was used for decoupling with a pulse length of 5.3 microseconds. $^1$H 90-degree pulse length of 2.9 microseconds was employed. All 19F (@ 14 kHz spinning speed) SSNMR experiments were conducted using the 500 MHz Bruker instrument. 19F data were acquired using a CP sequence. 64-256 K scans were collected for signal averaging. A contact time of 750 microseconds and a recycle delay of 7 seconds was used. $^1$H 90-degree pulse length of 3.54 microseconds was employed.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

The invention claimed is:

1. A process for preparing a crystalline polymorph comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol or n-propanol, and then cooling the mixture whereby a Form A crystalline polymorph that exhibits an X-ray powder diffraction pattern having characteristic peaks expressed in degrees 2-theta at approximately 5.7, 11.4, 17.2, 19.0, 19.7, and 24.4 is formed.

2. The process of claim 1 wherein ethanol or n-propanol are used with water.

3. The process of claim 1 wherein ethanol or n-propanol are used without water.

4. The process of claim 1 comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol in the presence of less than 40% of water.

5. The process of claim 1 further comprises seeding the mixture with crystalline (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide.

6. The process of claim 5, further comprises seeding the mixture with crystalline (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide as a crystalline THF solvate.

7. A process for preparing a crystalline polymorph comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol or n-propanol, and then cooling the mixture whereby a Form A crystalline polymorph is formed, wherein the Form A crystalline polymorph is characterized by the X-ray powder diffraction pattern substantially as shown in FIG. 4, or the X-ray powder diffraction peaks shown in Table 2, and a differential scanning calorimetry showing a melting endotherm at approximately 212 to 215° C.

8. The process of claim 7 wherein ethanol or n-propanol are used with water.

9. The process of claim 7 wherein ethanol or n-propanol are used without water.

10. The process of claim 7 comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol in the presence of less than 40% of water.

11. The process of claim 7 further comprises seeding the mixture with crystalline (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide.

12. The process of claim 7, further comprises seeding the mixture with crystalline (S)-2-((2-((S)-4-(difluoromethyl)-

2-oxooxazolidin-3-yl)-5,6-dihydrobenzo[f]imidazo[1,2-d][1,4]oxazepin-9-yl)amino)propenamide as a crystalline THF solvate.

13. A process for preparing a crystalline polymorph comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol or n-propanol, and then cooling the mixture whereby a Form A crystalline polymorph is formed, wherein the Form A crystalline polymorph is characterized by the $^{13}$C SSNMR (solid-state nuclear magnetic resonance) spectra substantially as shown in FIG. 7A, and the $^{19}$F SSNMR (solid-state nuclear magnetic resonance) spectra substantially as shown in FIG. 7B.

14. The process of claim 13 wherein ethanol or n-propanol are used with water.

15. The process of claim 13 wherein ethanol or n-propanol are used without water.

16. The process of claim 13 comprising heating a slurry of (S)-2-((2-((S)-4-(difluoromethyl)-2-oxooxazolidin-3-yl)-5,6-dihydrobenzo[f]imidazo[1,2-d][1,4]oxazepin-9-yl)amino)propanamide in ethanol in the presence of less than 40% of water.

17. The process of claim 13 further comprises seeding the mixture with crystalline (S)-2-((2-((S)-4-(difluoromethyl)-2-oxooxazolidin-3-yl)-5,6-dihydrobenzo[f]imidazo[1,2-d][1,4]oxazepin-9-yl)amino)propenamide.

18. The process of claim 13, further comprises seeding the mixture with crystalline (S)-2-((2-((S)-4-(difluoromethyl)-2-oxooxazolidin-3-yl)-5,6-dihydrobenzo[f]imidazo[1,2-d][1,4]oxazepin-9-yl)amino)propenamide as a crystalline THF solvate.

\* \* \* \* \*